United States Patent
Demassey et al.

(10) Patent No.: US 6,838,453 B2
(45) Date of Patent: Jan. 4, 2005

(54) ANTAGONIST DERIVATIVES OF THE VITRONECTIN RECEPTOR

(75) Inventors: Jacques Demassey, Montovrain (FR); Jean-Francois Gourvest, Claye Souilly (FR); Jean-Marie Ruxer, Issey les Moulineaux (FR); John Bernard Weston, Maisons Laffitte (FR); Jean-Michel LeFrancois, Le Raincy (FR)

(73) Assignee: Aventis Pharma S.A. (FR)

( * ) Notice: Subject to any disclaimer, the term of this patent is extended or adjusted under 35 U.S.C. 154(b) by 3 days.

(21) Appl. No.: 10/275,409

(22) PCT Filed: May 4, 2001

(86) PCT No.: PCT/FR01/01357
§ 371 (c)(1),
(2), (4) Date: Nov. 4, 2002

(87) PCT Pub. No.: WO01/85729
PCT Pub. Date: Nov. 15, 2001

(65) Prior Publication Data
US 2004/0225111 A1 Nov. 11, 2004

(30) Foreign Application Priority Data
May 9, 2000 (FR) .............................. 00 05859

(51) Int. Cl.$^7$ ..................... A61K 31/33; A61K 31/50; C07D 239/00; C07D 239/02
(52) U.S. Cl. ..................... 514/183; 514/247; 544/242; 544/330
(58) Field of Search ................. 514/183, 247; 544/242, 330

(56) References Cited

FOREIGN PATENT DOCUMENTS

| | | | |
|---|---|---|---|
| EP | 535521 | * | 4/1993 |
| EP | 0820988 | | 1/1998 |
| EP | 0820991 | | 1/1998 |
| WO | 9937621 | | 7/1999 |
| WO | 9945927 | * | 9/1999 |
| WO | 0018759 | | 4/2000 |

OTHER PUBLICATIONS

Fernandes et al, PubMed Abstract12082286, also cited as Biorheology, 39/1–2,237–46 (2002).*
McFarlane et al, PubMed Abstract 15034190, also cited as Endocrine,23/1,1–10(2004).*
Koobi et al, PubMed Abstract 15058982, also cited as Nephron. Exp. Nephrol. 96/3,91–8(2004).*
Cecil textbook of medicine, $20^{th}$ Edition, vol. 1, 1004–1010(1996).*
Uckun et al, Current Cancer Drug Targets,1,59–71(2001).*
Chemical Abstract DN 119:249940, also cited as EP535521.*
Chemical Abstract DN 131:214194.*
Gobbo et al, PubMed Abstract 15062975, also cited as Neuroscience, 125/2,317–27(2004).*
Lein et al, PublMed Abstract 14716014, also cited as Science, 303/5655,229–32(2004).*

* cited by examiner

Primary Examiner—Richard L. Raymond
Assistant Examiner—Sudhaker B. Patel
(74) Attorney, Agent, or Firm—Muserlian, Lucas and Mercanti

(57) ABSTRACT

The invention concerns vitronectin receptor antagonist compounds of formula (3): $R_1$—Y—A—B—D—E—F—G wherein $R_1$, Y, A, B, D, E, F, and G are as defined in the description, their physiologically acceptable salts and their prodrugs, methods for preparing compounds of formula (I), their use, in particular as medicine and pharmaceutical compositions containing them.

16 Claims, No Drawings

ANTAGONIST DERIVATIVES OF THE VITRONECTIN RECEPTOR

This application is a 371 of PCT/FR01/01358 filed May 4, 2001.

A subject of the present invention is new antagonist derivatives of the vitronectin receptor, their preparation process, their use as medicaments and the pharmaceutical compositions containing them.

A subject of the invention is the compounds of formula (I):

in which $R_1$, Y, A, B, D, E, F and G have the meanings indicated below, their physiologically acceptable salts and their prodrugs. The compounds of formula (I) are compounds having a pharmacological activity and can therefore be used as medicaments. These are antagonists of the vitronectin receptor and inhibitors of cell adhesion and they inhibit bone resorption mediated by the osteoclasts. They are therefore useful for the therapeutic or prophylactic treatment of diseases which are caused at least in part by an undesirable increase in bone resorption, for example osteoporosis. A subject of the invention is also the preparation process for the compounds of formula (I), their use, in particular as medicaments and the pharmaceutical compositions containing them.

The bone is constantly subjected to a dynamic process which includes bone resorption and bone formation. These processes are mediated via specialized cells. Bone formation is the result of the deposit of a mineral matrix by the osteoclasts and bone resorption is the result of the dissolution of this bone matrix by the osteoclasts. The majority of bone disorders are caused by a disturbed equilibrium between bone formation and bone resorption. Osteoporosis is characterized by a dry loss of this bone matrix. An activated mature osteoclast resorbs the bone after adhesion to the bone matrix via the secretion of proteolytic enzyme, and protons inside the adhesion zone, resulting in depressions or hollows on the bone surface which appear when the osteoclast detaches itself from the bone.

Studies have shown that the fixation of the osteoclast on the bone is mediated by receptors: the integrins. Integrins are a superfamily of receptors mediating the cell/cell and more particularly cell/matrix adhesion process, including in particular $\alpha_{IIb}\beta_3$ as a blood platelet receptor (fibrinogen) and $\alpha_v\beta_3$ as vitronectin receptor. The peptides containing the RGD unit as well as the anti $\alpha_v\beta_3$ antibodies are known for their ability to inhibit resorbtion of dentin and prevention of osteoclast adhesion on the mineralized matrices (Horton et al. Exp. Cell. Res. (1991), 195, 368). The peptide Echistatin, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411).

The $\alpha_v\beta_3$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta_3$ receptors expressed in the membrane of the osteoclasts are the basis of the adhesion/resorption process, contribute to the organization of the cell cytoskeleton, and are involved in osteoporosis. The $\alpha_v\beta_3$ receptors expressed in the smooth muscle cells of the aorta, stimulate their migration towards the neointima, which leads to the formation of arteriosclerosis and the occurrence of post-angioplastic recurrence of stenosis (Brown et al., cardiovascular Res. (1994), 28, 1815). The endothelial cells secrete growth factors which are mitogens for the endothelium and can contribute to the formation of new blood vessels (Angiogenesis).

The antagonists of $\alpha_v\beta_3$ integrin can therefore lead to a regression of cancerous tumors by inducing apoptosis of the angiogenic blood vessels. (Brook et al. Cell (1994) 79, 1157).

Cheresh et al (Science 1995, 270, 1500) have described anti-$\alpha_v\beta_3$ antibodies or antagonists of the $\alpha_v\beta_3$ receptor which inhibit the process of angiogenesis induced by bFGF in the rat eye, a property which can be used for the treatment of retinopathies, in particular in diabetics.

The Patent Application WO-A-94/12181 describes aromatic or non-aromatic substituted systems and WO-A-94/08577 describes substituted heterocycles as antagonists of the fibrinogen receptor and inhibitors of platelet aggregation. EP-A-528586 and EP-A-528587 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. DE-A-19654483 describes tyrosine derived antagonists of the vitronectin receptor. DE-A-19629816.4 claims cycloalkyl derivatives as antagonists of the vitronectin receptor. Other investigations have made it possible to show that the derivatives of formula (I), containing in alpha or beta position of the carboxy which can be represented by $R_6$, an amine substituted by a heterocycle (—NH—R5) show marked activity as antagonists of the vitronectin receptor and of bone resorption mediated via the osteoclasts.

A subject of the invention is the compounds of formula (I):

in all their isomer forms, alone or in a mixture, as well as their physiologically acceptable addition salts, in which $R_1$ represents $R_3$—C(=NR$_2$)—NR$_2$—, $R_2R_3$N—C(=NR$_2$)—, $R_2R_3$N—C(=NR$_2$)—NR$_2$— or a monocyclic or polycyclic system, each ring being constituted by 4 to 10 aromatic or non aromatic members, the ring or at least one of the rings containing 1 to 4 heteroatoms chosen from N, O or S, substituted or non substituted by the $R_{10}$, $R_{11}$, $R_{12}$ and $R_{13}$ groups;

Y represents a direct bond or —NR$_2$—

A represents a single bond, —(C$_1$-C$_8$)alkylene-, —NR$_2$—C(O)—NR$_2$—, —NR$_2$—C(O)O—, —NR$_2$—C(O)—S—, —NR$_2$—C(S)—NR$_2$—, —NR$_2$—C(S)—O—, —NR$_2$—C(S)—S—, —NR$_2$—S(O)n-NR$_2$—, —NR$_2$—S(O)n-O—, —NR$_2$—S(O)$_n$—, —(C$_3$-C$_{12}$)-cycloalkylene-, —C≡C—, —NR$_2$—C(O)—, —C(O)—NR$_2$—, —(C$_5$-C$_{14}$)-arylene-C(O)—NR$_2$—, —O—, —S(O)$_n$—, —(C$_5$-C$_{14}$)-arylene-, —CO—, —(C$_5$-C$_{14}$)-arylene-CO—, —NR$_2$—, —SO$_2$—NR$_2$—, —CO$_2$—, —CR$_2$=CR$_3$—, —(C$_5$-C$_{14}$)-arylene-S(O)$_n$—, these groups being able if appropriate to be substituted on both sides by an alkylene group;

B represents a single bond, —(C$_1$-C$_8$)-alkylene-, —CR$_2$=CR$_3$— or —C≡C— which if appropriate can be substituted on both sides by an alkylene group;

D represents a single bond, —(C$_1$-C$_8$)alkylene-, —O—, —NR$_2$—, —CONR$_2$—, —NR$_2$—CO—, —NR$_2$—C(O)—

$NR_2$—, —$NR_2$—C(S)—$NR_2$—, —OC(O)—, —C(O)O—, —CO—, —CS—, —$S(O)_2$—, —$S(O)_2$—$NR_2$—, —$NR_2$—S(O)—, —$NR_2$—$S(O)_2$—, —S—, —$CR_2$=$CR_3$—, —C≡C—, or —CH(OH)—, these groups being able if appropriate to be substituted on both sides by an alkylene group;

E represents a monocyclic or polycyclic system, each ring being constituted by 4 to 10 aromatic or non aromatic members containing 0 to 4 heteroatoms chosen from N, O or S and substituted or non substituted by the $R_{10}$, $R_{11}$, $R_{12}$ and $R_{13}$ groups;

F has the same values as D;

G represents a

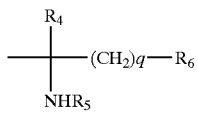

group, q representing 0 or 1

$R_2$ and $R_3$, identical or different represent H, $(C_1-C_8)$-alkyl-, if appropriate substituted by one or more halogen atoms, $(C_3-C_{12})$-cycloalkyl-, $(C_3-C_{12})$-cycloalkyl-$(C_1-C_8)$-alkyl-, $(C_5-C_{14})$-aryl-, $(C_5-C_{14})$-aryl-$(C_1-C_8)$-alkyl, —$NH_2$, $(R_8O)R_8NR_7$—, $R_8OR_7$—, $R_8OC(O)R_7$—, $R_8$—$(C_5-C_{14})$-aryl-$R_7$—, $R_8R_8NR_7$—, HO—$(C_1-C_8)$alkyl-$NR_8$—$R_7$—, $R_8R_8NC(O)R_7$—, $R_8C(O)NR_2R_7$—, $R_8C(O)R_7$—, $R_8R_8N$—C(=$NR_8$)—, $R_8R_8N$—C(=$NR_8$)—$NR_2$—, $(C_1-C_{18})$-alkylcarbonyloxy-, $(C_1-C_6)$ -alkyloxycarbonyl-;

$R_4$ represents H, fluorine, $(C_1-C_8)$-alkyl-, $(C_3-C_{12})$-cycloalkyl-$(C_1-C_8)$alkyl-, $(C_5-C14)$-aryl, $(C_5-C_{14})$-aryl-$(C_1-C_8)$alkyl-, the alkyl remainder being able to be substituted by one or more fluorines;

$R_5$ represents a monocyclic or polycyclic system, each ring being constituted by 4 to 10 aromatic or non-aromatic members, the ring or at least one of the rings containing 1 to 4 heteroatoms chosen from N, O or S, substituted or non-substituted by the groups chosen from $R_{10}$, $R_{11}$, $R_{12}$ and $R_{13}$;

$R_6$ represents —C(O)$R_9$, —C(S)$R_9$, $S(O)_nR_9$, $P(O)(R_9)_n$, or a heterocycle with 4 to 8 members containing 1 to 4 heteroatoms chosen from N, O and S such as tetrazole, imidazole, pyrazole, oxazole or thiadiazole;

$R_7$ represents a direct bond or a $(C_1-C_8)$-alkylene-;

$R_8$ represents H, $(C_1-C_8)$-alkyl-, $(C_3-C_{12})$-cycloalkyl-, $(C_3-C_{12})$-cycloalkyl-$(C_1-C_8)$alkyl-, $(C_5-C_{14})$-aryl-, $(C_5-C_{14})$-aryl-$(C_1-C_8)$-alkyl, in which the alkyl remainder is, if appropriate, substituted by one or more fluorine atoms;

$R_9$ represents OH, $(C_1-C_8)$-alkoxy-, $(C_5-C_{14})$-aryl-$(C_1-C_8)$alkyloxy-, $(C_5-C_{14})$-aryloxy-, $(C_1-C_8)$-alkylcarbonyloxy$(C_1-C_4)$alkyloxy-, $(C_5-C_{14})$-aryl-$(C_1-C_8)$-alkylcarbonyloxy$(C_1-C_4)$ alkyloxy-, $NH_2$, mono or di-$(C_1-C_8$-alkyl)-amino-, $(C_5-C_{14})$-aryl-$(C_1-C_8)$-alkylamino-, $(C_1-C_8)$dialkylaminocarbonyl methyloxy-, $(C_5-C_{14})$-aryl-$(C_1-C_8)$-dialkylaminocarbonyl methyloxy- or $(C_5-C_{14})$arylamino- or a D or L aminoacid remainder.

$R_{10}$, $R_{11}$, $R_{12}$, $R_{13}$, identical or different, independently from one another, represent H, $(C_1-C_8)$-alkyl-, if appropriate substituted by one or more halogen atoms, $(C_3-C_{12})$-cycloalkyl-, $(C_3-C_{12})$-cycloalkyl-$(C_1-C_8)$-alkyl-, $(C_5-C_{14})$-aryl-, $(C_5-C_{14})$-aryl-$(C_1-C_8)$-alkyl-, $NH_2$, $(R_8O)R_8NR_7$—, $R_8OR_7$—, $R_8OC(O)R_7$—, $R_8$—$(C_5-C_{14})$-aryl-$R_7$—, $R_8R_2NR_7$—, HO—$(C_1-C_8)$alkyl-$NR_2$—$R_7$—, $R_8R_2NC(O)R_7$—, $R_8C(O)NR_2R_7$—, $R_8C(O)R_7$—, $R_2R_3N$—C(=$NR_2$)—, —$R_2R_3N$—C(=$NR_2$)—$NR_2$—, =O, =S, halogen, —$NO_2$; $R_8SO_2R_7$—, $R_8NHSO_2R_7$— or $R_8R_2NSO_2R_7$—;

n represents 1 or 2.

All the radicals which can be found several times in the compounds of formula (I), for example the $R_2$ radical, are independent from one another and can be identical or different.

The alkyl radicals can be linear or branched, saturated or mono- or poly-unsaturated. This also applies when they carry a substituent or when they are included in groups such as for example alkoxy, alkoxycarbonyl or aralkyl.

By $(C_1-C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylepentyl, 2,3,4-trimethylhexyl, sec-butyl, tert-butyl, tert-pentyl. Among the preferred radicals methyl, ethyl, n-propyl, isopropyl, n-butyl, isobutyl, and tert-butyl can be mentioned.

The divalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals are for example the alkenyl radicals such as vinyl, 1-propenyl, allyl, butenyl, 3-methyl-2-butenyl or the alkynyl radicals such as ethynyl, 1-propynyl or propargyl.

By unsaturated divalent alkylene radicals is meant the alkenylene and alkynylene radicals which can also be linear or branched. It concerns for example vinylene, propenylene, ethynylene or propynylene radicals.

When A represents a group which can be substituted on both sides by an alkylene group, it concerns for example —$(C_1-C_8)$-alkylene-CONH—$(C_1-C_8)$-alkylene-, —$(C_1-C_8)$-alkylene-CONH— or —CONH—$(C_1-C_8)$-alkylene-.

When B or D represent a group which can be substituted on both sides by an alkylene group, it concerns for example —$CH_2$—C≡C—$CH_2$ or —$CR_2$=$CR_3$—$CH_2$—.

The cycloalkyl radicals can be monocyclic, bicyclic or tricyclic. They are for example cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl radicals which can if appropriate be substituted for example by an alkyl containing 1 to 4 carbon atoms. As substituted cycloalkyl radicals, 4 methylcyclohexyl and 2,3-dimethylecyclo-hexyl can be mentioned.

The bicycloalkyl and tricycloalkyl radicals can be non-substituted or substituted in any position, for example by one or more oxo groups and/or 1 or more identical or different alkyl groups such as methyl or isopropyl and preferably methyl. The junction bond of the bi or tricyclic radical can be situated in all positions of the molecule. The bond can be situated at the bridged carbon atom or one of the other carbon atoms. This bond can also take any position from the point of view of the stereochemistry, for example exo or endo. As an example of bicycloalkyl or tricycloalkyl radicals, camphanyl, bornyl, adamantyl such as 1-adamantyl or 2-adamantyl, caranyl, epiisobornyl, epibornyl, norbornyl or norpinanyl can be mentioned.

By halogen is meant fluorine, chlorine, bromine or iodine.

By the term $(C_5-C_{14})$-aryl is meant either the heterocyclic $(C_5-C_{14})$-aryl radicals (=$(C_5-C_{14})$-heteroaryl), in which the carbon atoms of the ring are replaced by a heteroatom such as nitrogen, oxygen or sulphur, or the carbocyclic $(C_6-C_{14})$-aryl radicals.

Among the carbocyclic $(C_6-C_{14})$-aryl radicals, phenyl, naphthyl, biphenylyl, anthryl or fluorenyl and more particularly 1-naphthyl, 2-naphthyl and phenyl can be mentioned.

Unless indicated to the contrary, the aryl radicals, in particular phenyl, can be non-substituted or substituted by one or more identical or different radicals chosen from ($C_1$–$C_8$)-alkyl, in particular ($C_1$–$C_4$)alkyl, ($C_1$–$C_8$)-alkoxy, hydroxy, halogen such as fluorine, chlorine and bromine, nitro, amino, trifluoromethyl, methylenedioxy, cyano, aminocarbonyl, carboxy, ($C_1$–$C_4$)-alkoxycarbonyl, phenyl, phenoxy, benzyl and benzyloxy. In general, 2 nitro groups at the most can be used in the compounds of formula (I) according to the invention.

In the case of monosubstituted phenyl, the substituent can be situated in position 2, 3 or 4, and preferably in position 3 or 4. In the case where the phenyl is di-substituted, the substituents can be in position 2, 3 or 2, 4 or 2, 5 or 2, 6 or 3, 4 or 3, 5. Preferably, in the di-substituted phenyls, the two substituents are in position 3, 4. When this phenyl is tri-substituted the positions are the following: 2, 3, 4 or 2, 3, 5 or 2, 3, 6 or 2, 4, 5 or 2, 4, 6 or 3, 4, 5. In the same way, the naphthyl radicals or other aryl radicals can be substituted in any position, for example the 1-naphthyl radical in position 2-, 3-, 4-, 5-, 6-, 7-, and 8 and the 2-naphthyl radical in position 1-, 3-, 4-, 5-, 6-, and 7.

The ($C_5$–$C_{14}$)-aryl group can also represent a monocyclic or polycyclic aromatic system in which 1, 2, 3 or 4 carbon atoms of the ring are replaced by heteroatoms, in particular, identical to or different from the group constituted by nitrogen, oxygen and sulphur. Among the heterocyclic ($C_5$–$C_{14}$)-aryls groups (=($C_5$–$C_{14}$)-heteroaryl) there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups, or also benzo-condensed, cyclopenta-, cyclohexa-, or cyclohepta- condensed derivatives of these radicals. The heterocyclic system can be substituted by the same substituents mentioned above for the carbocyclic system.

The definition of E includes the carbocyclic or heterocyclic aryles as defined above and the definition of $R_1$ or $R_5$ includes the heterocyclic aryles as defined above.

The optically active carbon atoms contained in the compounds of formula (I) can independently from one another show the R configuration or the S configuration.

The compounds of formula (I) can be in the form of pure enantiomers or of pure diastereoisomers or in the form of a mixture of enantiomers, for example in the form of racemates or diastereoisomer mixtures.

A subject of the present invention is therefore pure enantiomers, mixtures of these enantiomers, pure diastereoisomers and mixtures of these diastereoisomers.

The invention includes mixtures of two or more than two stereoisomers of formula (I) and all the ratios of these stereoisomers in the said mixtures.

The compounds of formula (I) can, if appropriate, be present in the form of E or Z isomers. A subject of the invention is therefore pure E isomers, pure Z isomers and E/Z mixtures in any ratio.

The invention also relates to all the tautomer forms of the compounds of formula (I), for example concerning the form represented by formula (I), with A=—NHCO—, Y=single bond and $R_1$=$R_2R_3$N—C(=NH)—, the form in which acylguanidine is present in the form of a —CO—N=C(NHR$_2$)—NR$_2$R$_3$ group and all the other forms which differ by the different position of the hydrogen atom are considered.

The diastereoisomers, including the E/Z isomers can be separated into individual isomers, for example by chromatography. The racemates can be separated into two enantiomers by current methods such as chiral phase chromatography or by resolution methods.

The physiologically acceptable salts of the compounds of formula (I) are in particular salts which can be used pharmaceutically or non-toxic salts, or salts which can be used physiologically.

When the compounds of formula (I) contain an acid group such as carboxylic acid, they are for example salts of alkali or alkaline-earth metals such as sodium, potassium, magnesium, calcium salts, and also the salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids for example with inorganic acids such as hydrochloric, sulphuric, phosphoric acid or with organic carboxylic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of Zwiterions (betaines), which are also included in the present invention.

The physiologically acceptable $Q^-$ anion which may be contained in the compounds of formula (I) containing a charged ammonium group, is preferably a monovalent anion or a polyvalent anion equivalent of an organic or inorganic, non-toxic, physiologically acceptable and in particular pharmaceutically acceptable acid, for example the anion or an anion equivalent of one of the acids mentioned above which can be used for the formation of the addition salts. $Q^-$ for example can be one of the anions (or anion equivalent) of a group chosen from chlorine, sulphate, phosphate, acetate, trifluoroacetate, citrate, benzoate, maleate, fumarate, tartrate, methanesulphonate and para-toluenesulphonate.

The salts of the compounds of formula (I) can be obtained by standard methods known to a person skilled in the art, for example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as medicaments, but can be used as intermediate products to implement the subsequent chemical modifications in the compounds of formula (I) or as starting products for the preparation of physiologically acceptable salts.

The present invention also includes all the solvates of the compounds of formula (I) for examples the hydrates, the solvates formed with alcohols, and all the derivatives of the compounds of formula (I), for example the esters, prodrugs and other physiologically acceptable derivatives, as well as the metabolites of the compounds of formula (I).

A subject of the invention is also the prodrugs of the compounds of formula (I) which can be converted to compounds of formula (I) in vivo under physiological conditions. The prodrugs of the compounds of formula (I), namely the chemically modified derivatives of the compounds of formula (I), in order to obtain the improved properties in a desired fashion are known to a person skilled in the art.

In order to have more information on the type of prodrug envisaged in the present invention, the following books can be mentioned: Fleicher et al., Advanced Drug Delivery Review 19 (1996) 115–130; Design of prodrugs, H. Bundgaard, Ed., Elsevier, 1985; H. Bungaard, Drugs of the Future 16 (1991) 443; Saulnier et al. Bioorg. Med. Chem. Lett. 4 (1994) 1985; Safadi et al. Pharmaceutical Res. 10 (1993) 1350. Among the appropriate prodrugs of the compounds of formula (I) the following can preferably be mentioned:

the prodrugs in the form of esters of the carboxylic groups, in particular of the $R_6=COR_9$ group, when $R_9$ is a hydroxy group.

the prodrugs in the form of acyl and carbamate for the groups containing an acylable nitrogen such as the amino groups and in particular guanidine.

In the acylated prodrugs or in the form of carbamate, a hydrogen atom situated on the nitrogen atom is replaced one or more times, for example twice by an acyl or carbamate group. Among the preferred acyl or carbamate groups, the $R_{14}CO—$, $R_{15}OCO—$ groups, in which $R_{14}$ is a hydrogen or a $(C_1–C_{18})$-alkyl, $(C_3–C_{14})$-cycloalkyl, $(C_3–C_{14})$-cycloalkyl-$(C_1–C_8)$-alkyl, $(C_5–C_{14})$-aryl radical, in which 1 to 5 carbon atoms can be replaced by heteroatoms such as N,O,S or $(C_5–C_{14})$-aryl-$(C_1–C_8)$alkyl, in which 1 to 5 carbon atoms in the aryl part can be replaced by heteroatoms such as N,O,S and $R_{15}$ has the same values as $R_{14}$ with the exception of hydrogen can be mentioned.

A more particular subject of the invention is the compounds of formula (I) as defined above in which G represents a:

group, $R_5$ being as defined above.

A particular subject of the invention is the compounds of formula (I), in which $R_5$ is a heterocycle chosen from

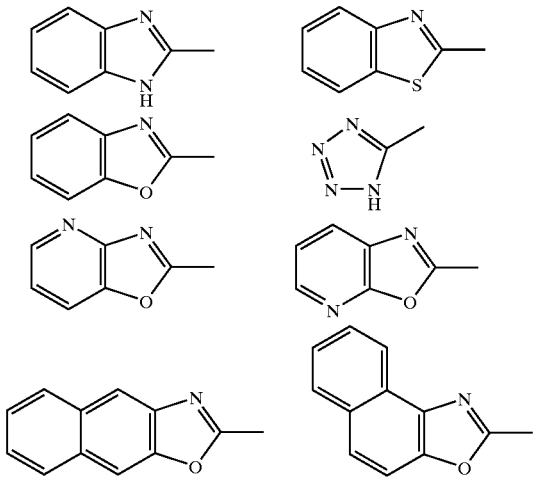

said heterocycles being substituted or non substituted by $R_{10}$, $R_{11}$, $R_{12}$ or $R_{13}$.

A more particular subject of the invention is the compounds of formula (I) as defined above in which:

Y represents a single bond or NH
$R_1$ is such as defined previously.
A represents a single bond, —CH$_2$—, —CH$_2$CH$_2$—, —NHCO—NH—, —NHC(O)—O—, —NHC(O)—S—, —NHC(S)—NH—, —NHC(S)—O—, —NHC(S)—S—, —NHSO—NH—, —NHS(O)—O—, —NHS(O)—, -cyclohexylene-, —C≡C—, —NHC(O)—, —C(O)NH—, -Ph-C(O)NH—, —O—, —S—, —S(O)—, —SO$_2$—, -phenylene-, —C(O)—, -PhC(O)—, —NH—, —SO$_2$—NH—, —C(O)—O—, —CH=CH—, -Ph-S(O)—, -Ph-S(O)—O—, —CH$_2$—CONH—CH$_2$—, —CH$_2$—CONH—, —CONH—CH$_2$—, —NHCO—CH$_2$—, —CH$_2$—NHCO—, —CH$_2$—NHCO—CH$_2$—;

B represents a single bond, —CH$_2$—, —CH$_2$CH$_2$—, —CH=CH—, —C≡C—, —C≡C—CH$_2$—, CH$_2$—C≡C—, —CH=CH—CH$_2$—, —CH$_2$—CH=CH—;

D represents a single bond, —CH$_2$—, —CH$_2$CH$_2$—, —O—, —NH—, —CONH—, —NHCO—, —NHCONH—, —O—C(O)—, —C(O)—O—, —CO—, —SO$_2$—, —SO$_2$NH—, —NHSO$_2$—, —S—, —CH=CH—, —C≡C—, —CH(OH)—;

E is a phenyl substituted or non-substituted by the $R_{10}$, $R_{11}$, $R_{12}$ and $R_{13}$ groups as defined previously F has the same values as D;

G represents a —CH(NHR$_5$)—COOH group in which $R_5$ is as defined previously.

A particular subject of the invention is a compound of formula (Ia):

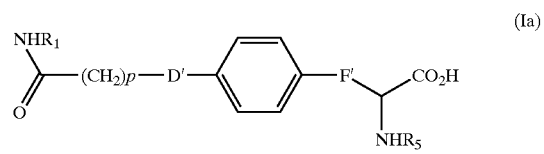

in which, D' represents an oxygen atom or a single bond, F' represents a —CH$_2$— or —CONH—CH$_2$— group, $R_1$ and $R_5$ are as defined previously and p is equal to 1 to 8.

A particular subject of the invention is the compounds of formulae (Ib) in which:

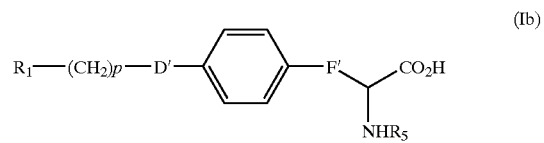

in which D' represents an oxygen atom or a single bond, F' represents a —CH$_2$— or —CONH—CH$_2$— group, $R_1$ and $R_5$ are as defined previously and p is equal to 1 to 8.

A particular subject of the invention is a compound of formula (Ia) as defined previously in which D' represents an oxygen atom, p is comprised between 2 and 4 and F' is a —CH$_2$— group.

A particular subject of the invention is a compound of formula (Ia) as defined previously in which D' represents a single bond, p is comprised between 2 and 5 and F' is a —CONH—CH$_2$— group.

A more particular subject of the invention is the compounds of formula (I), (Ia) or (Ib) in which, $R_1$ is a heterocycle chosen from

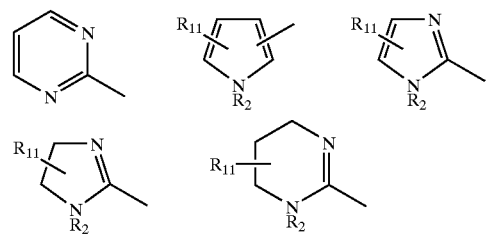

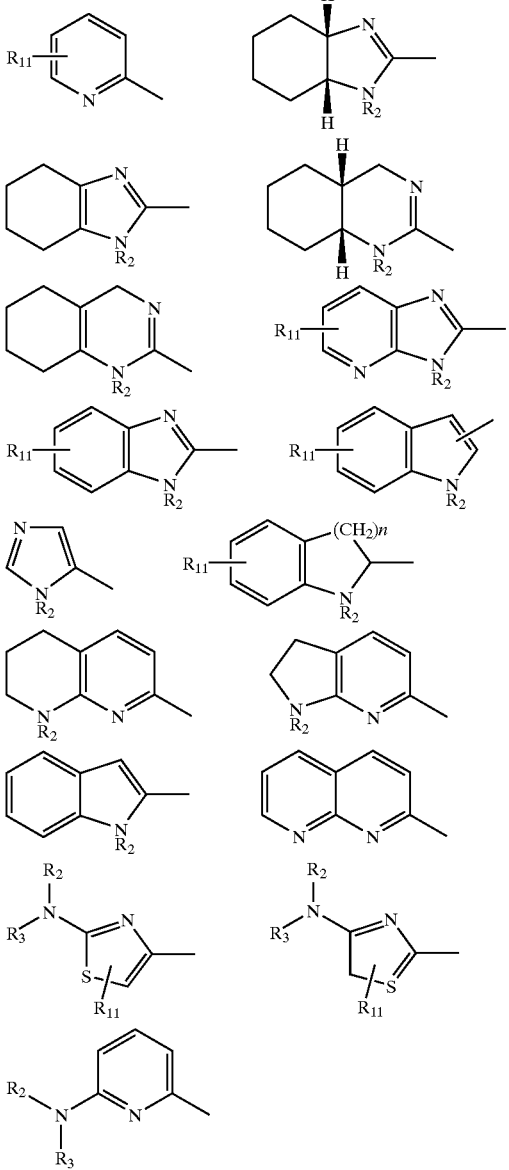

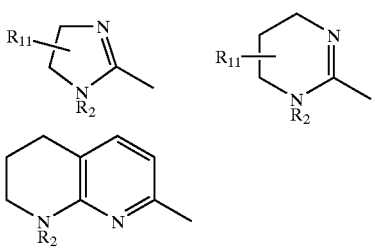

$R_2$ and $R_{11}$ being as defined previously.

A quite particular subject of the invention is the compounds of formulae (I), (Ia) or (Ib) as defined previously in which $R_5$ represents a heterocycle as defined previously substituted by one or more groups chosen from phenyl, benzyl, chlorine, bromine, fluorine, nitro, carboxy, methyloxycarbonyl, phenylaminosulphonyl, methylphenylaminosulphonyl, $(C_1–C_2)$-alkyl optionally substituted by one or more chlorine, bromine or fluorine atoms such as trifluoromethyl.

A quite particular subject of the invention is the compounds of formulae (I), (Ia) or (Ib) as defined previously in which $R_5$ represents a heterocycle as defined previously substituted by one or more halogen atoms chosen from chlorine, bromine and fluorine.

A subject of the invention is also the compounds of formula (I) the names of which follow:

N-[1-(phenylmethyl)-1H-tetrazol-5-yl]-O-[3-(5,6,7,8-tetrahydro-1,8-naphthyridin-2-yl)propyl]-L-tyrosine;
N-(2-benzothiazolyl)-O-[3-(5,6,7,8-tetrahydro-1,8-naphthyridin-2-yl)propyl]-L-tyrosine;
N-(2-benzoxazolyl)-O-[3-(5,6,7,8-tetrahydro-1,8-naphthyridin-2-yl)propyl]-L-tyrosine;
N-[5-methoxy-1H-benzimidazol-2-yl]-O-[4-oxo-4-[(1,4,5,6-tetrahydro-2-pyrimidinyl)amino]butyl]-L-tyrosine;
N-[5-methyl-1H-benzimidazol-2-yl]-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-[1-(phenylmethyl)-1H-tetrazol-5-yl]-L-tyrosine;
N-(2-benzoxazolyl)-O-[4-oxo-4-[(1,4,5,6-tetrahydro-2-pyrimidinyl)amino]butyl]-L-tyrosine;
N-(2-benzothiazolyl)-O-[4-oxo-4-[(1,4,5,6-tetrahydro-2-pyrimidinyl)amino]butyl]-L-tyrosine;
N-[6-bromo-2-benzothiazolyl]-O-[4-oxo-4-[(1,4,5,6-tetrahydro-2-pyrimidinyl)amino]butyl]-L-tyrosine;
N-(5-bromo-7-fluoro-2-benzoxazolyl)-O-[4-oxo-4-[(1,4,5,6-tetrahydro-2-pyrimidinyl)amino]butyl]-L-tyrosine;
N-(5-bromo-2-benzoxazolyl)-3-[[4-[3-oxo-3-[(1,4,5,6-tetrahydro-2-pyrimidinyl)amino]propyl]benzoyl]amino]-L-alanine;
N-(6-bromo-2-benzothiazolyl)-3-[[4-[3-oxo-3-[(1,4,5,6-tetrahydro-2-pyrimidinyl)amino]propyl]benzoyl]amino]-L-alanine;
N-(7-fluoro-2-benzoxazolyl)-O-[4-oxo-4-[(1,4,5,6-tetrahydro-2-pyrimidinyl)amino]butyl]-L-tyrosine;
N-(6-fluoro-2-benzoxazolyl)-O-[4-oxo-4-[(1,4,5,6-tetrahydro-2-pyrimidinyl)amino]butyl]-L-tyrosine;
N-(5-fluoro-2-benzoxazolyl)-O-[4-oxo-4-[(1,4,5,6-tetrahydro-2-pyrimidinyl)amino]butyl]-L-tyrosine;
N-(7-chloro-2-benzoxazolyl)-O-[4-oxo-4-[(1,4,5,6-tetrahydro-2-pyrimidinyl)amino]butyl]-L-tyrosine;
N-(6-chloro-2-benzoxazolyl)-O-[4-oxo-4-[(1,4,5,6-tetrahydro-2-pyrimidinyl)amino]butyl]-L-tyrosine;
N-(5-chloro-2-benzoxazolyl)-O-[4-oxo-4-[(1,4,5,6-tetrahydro-2-pyrimidinyl)amino]butyl]-L-tyrosine;
N-(5-bromo-2-benzoxazolyl)-O-[4-oxo-4-[(1,4,5,6-tetrahydro-2-pyrimidinyl)amino]butyl]-L-tyrosine;
N-(naphth[2,3-d]oxazol-2-yl)-O-[4-oxo-4-[(1,4,5,6-tetrahydro-2-pyrimidinyl)amino]butyl]-L-tyrosine;
N-(naphth[1,2-d]oxazol-2-yl)-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-(5-phenyl-2-benzoxazolyl)-L-tyrosine;
N-(6-nitro-2-benzoxazolyl)-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-[5-(trifluoromethyl)-2-benzoxazolyl]-L-tyrosine;
N-(oxazolo[5,4-b]pyridin-2-yl)-O-[4-oxo-4-[(1,4,5,6-tetrahydro-2-pyrimidinyl)amino]butyl]-L-tyrosine;
N-(oxazolo[4,5-b]pyridin-2-yl)-O-[4-oxo-4-[(1,4,5,6-tetrahydro-2-pyrimidinyl)amino]butyl]-L-tyrosine;

O-[4-oxo-4-[(1,4,5,6-tetrahydro-2-pyrimidinyl)amino]
butyl]-N-[5-(trifluoromethyl)-oxazolo[4,5-b]pyridin-2-
yl]-L-tyrosine;
N-(6,7-difluoro-2-benzoxazolyl)-O-[4-oxo-4-[(1,4,5,6-
tetrahydro-2-pyrimidinyl)amino]butyl]-L-tyrosine;
N-(5,7-dichloro-2-benzoxazolyl)-O-[4-oxo-4-[(1,4,5,6-
tetrahydro-2-pyrimidinyl)amino]butyl]-L-tyrosine;
N-(5,7-dichloro-6-methyl-2-benzoxazolyl)-O-[4-oxo-4-[(1,
4,5,6-tetrahydro-2-pyrimidinyl)amino]butyl]-L-tyrosine;
N-[5-[(phenylamino)sulphonyl]-2-benzoxazolyl]-O-[4-oxo-
4-[(1,4,5,6-tetrahydro-2-pyrimidinyl)amino]butyl]-L-
tyrosine;
N-[5-[(N-methylphenylamino)sulphonyl]-2-benzoxazolyl]-
O-[4-oxo-4-[(1,4,5,6-tetrahydro-2-pyrimidinyl)amino]
butyl]-L-tyrosine;
N-(6-chloro-2-benzothiazolyl)-O-[4-oxo-4-[(1,4,5,6-
tetrahydro-2-pyrimidinyl)amino]butyl]-L-tyrosine;
N-(7-bromo-2-benzothiazolyl)-O-[4-oxo-4-[(1,4,5,6-
tetrahydro-2-pyrimidinyl)amino]butyl]-L-tyrosine;
N-(5-bromo-2-benzothiazolyl)-O-[4-oxo-4-[(1,4,5,6-
tetrahydro-2-pyrimidinyl)amino]butyl]-L-tyrosine;
N-(1H-benzimidazol-2-yl)-O-[4-oxo-4-[(1,4,5,6-
tetrahydro-2-pyrimidinyl)amino]butyl]-L-tyrosine;
N-(5-nitro-2-benzoxazolyl)-O-[4-oxo-4-[(1,4,5,6-
tetrahydro-2-pyrimidinyl)amino]butyl]-L-tyrosine;
N-(4-nitro-2-benzoxazolyl)-O-[4-oxo-4-[(1,4,5,6-
tetrahydro-2-pyrimidinyl)amino]butyl]-L-tyrosine;
N-(6-ethylsulphonyl-2-benzoxazolyl)-O-[4-oxo-4-[(1,4,5,6-
tetrahydro-2-pyrimidinyl)amino]butyl]-L-tyrosine;
N-(4,5,6,7-tetrafluoro-2-benzoxazolyl)-O-[4-oxo-4-[(1,4,5,
6-tetrahydro-2-pyrimidinyl)amino]butyl]-L-tyrosine;
N-(4-methyl-2-benzoxazolyl)-O-[4-oxo-4-[(1,4,5,6-
tetrahydro-2-pyrimidinyl)amino]butyl]-L-tyrosine;
N-(5-methoxy-2-benzoxazolyl)-O-[4-oxo-4-[(1,4,5,6-
tetrahydro-2-pyrimidinyl)amino]butyl]-L-tyrosine;
N-(4-hydroxy-2-benzoxazolyl)-O-[4-oxo-4-[(1,4,5,6-
tetrahydro-2-pyrimidinyl)amino]butyl]-L-tyrosine;
N-(6-hydroxy-2-benzoxazolyl)-O-[4-oxo-4-[(1,4,5,6-
tetrahydro-2-pyrimidinyl)amino]butyl]-L-tyrosine;
N-(2-benzoxazoyl)-3-[[4-[3-oxo-3- [(1,4,5,6-tetrahydro-2-
pyrimidinyl)amino]propyl]benzoyl]amino]-L-alanine;
N-(7-fluoro-2-benzoxazolyl)-3-[[4-[3-oxo-3-[(1,4,5,6-
tetrahydro-2-pyrimidinyl)amino]propyl]benzoyl]amino]-
L-alanine;
N-(7-fluoro-2-benzoxazolyl)-O-[4-oxo-4-[(5-hydroxy-1,4,
5,6-tetrahydro-2-pyrimidinyl)amino]butyl]-L-tyrosine.

A subject of the present invention is also a process for the preparation of the compounds of formula (I). The compounds can generally be prepared, for example during convergent synthesis by coupling two or more fragments which can be derived by retrosynthesis of the compounds of formula (I). In order to avoid the functional groups leading to undesirable or secondary reactions during each stage of synthesis, it can be advantageous or necessary during the synthesis of the compounds of formula (I), to introduce the functional groups in the form of precursors which are subsequently converted to desired functional groups or to temporarily block these functional groups by implementing a protective group strategy suitable for the synthesis which is known to a person skilled in the art (Greene, Wuts protective Group in Organic Synthesis, Wiley 1991).

The compounds of formula (I) can therefore be prepared, for example, by coupling, in the presence of a Lewis acid, a carboxylic acid or a carboxylic acid derivative of formula (II):

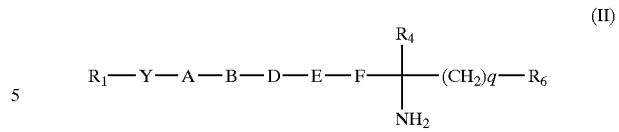

in which $R_1$, Y, A, B, D, E, F, $R_4$, $R_6$ and q are as defined above for the formula (I), and where, if appropriate, the functional groups are in the form of precursors or in protected form, with a heterocycle of formula $R_5$-Hal or $R_5$—SMe in which $R_5$ being as defined above in formula (I) and Hal representing a halogen, and where, if appropriate, the functional groups are in the form of precursors or in protected form, said functional groups optionally present in the form of a precursor or in protected form, being subsequently converted into groups present in the compounds of formula (I).

When a halogenated derivative ($R_5$—Hal) is reacted, the reaction is preferably carried out in pyridine or toluene under reflux.

When a thioalkylated derivative such as $R_5$—Sme is reacted, the reaction is carried out in the presence of $HgCl_2$ or of $Hg(OAc)_2$ under reflux.

When $R_5$ represents a benzimidazole, the preparation can take place as follows: an aryl isothiocyanate substituted in alpha position by a nitro group is reacted in the presence of a hindered base, in order to obtain the intermediate thiourea, then the nitro group is reduced and finally cyclization is carried out in the presence of $HgCl_2$ or $Hg(OAc)_2$.

When $R_5$ represents a benzothiazole, the preparation can take place as follows: an optionally substituted aryl isothiocyanate is reacted in the presence of a hindered base, in order to obtain the intermediate thiourea, then cyclization is carried out in the presence of $SO_2Cl_2$.

As a variant, the introduction of $R_5$ can be carried out prior to the introduction of $R'_1$ according to the following diagram:

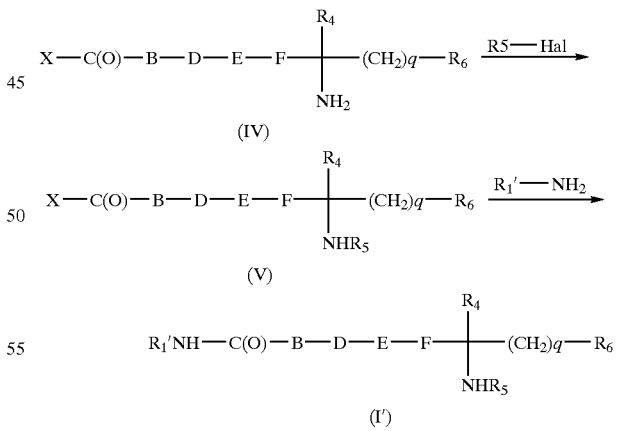

$R'_1$ corresponding to the compounds as defined for $R_1$ such as $R_2R_3$—C(=NR_2)— or a heterocycle as defined previously.

As a variant, the introduction of $R_5$ can be carried out at various stages of the process as shown by the examples below.

The COX group in formula (IV) is preferably the carboxylic acid group or an activated derivative of carboxylic acid. X, for example is hydroxyl or halogen, in particular, chlorine or bromine, alkoxy, preferably methoxy or ethoxy, aryloxy, for example phenoxy, pentafluorophenyloxy, phenylthio, methylthio, 2-pyridylthio or a nitrogenous heterocycle linked via a hydrogen atom, in particular nitrogen such as 1-imidazolyl for example. X can also be for example ($C_1$-$C_4$)-alkyl-O—CO—O— or tolylsulphonyloxy and the activated acid derivative can be a mixed anhydride.

If X is a hydroxyl, and therefore if the guanidine of formula ($R_1$—$NH_2$) reacts with a carboxylic acid of formula (IV), then the carboxylic acid is activated first.

The activation can be carried out for example with dicyclohexylcarbodiimide (DCCI) or with O-((cyano (ethoxycarbonyl)-methylene)amino)-1,1,3,3-tetramethyluronium tetrafluoroborate (TOTU; König et al, Proc. 21st Europ. Peptide Symp. 1990 (Eds Giralt, Andreu), Escom, Leiden 1991, p.243) or other activating agents currently used in peptide synthesis.

As well as the free guanidines of formula ($R'_1$—$NH_2$), the guanidine salts can also be used in the reaction with the compounds of formulae (IV) or (V), the free guanidines being formed in-situ or in a separate stage using a base.

The reaction of an activated derivative of carboxylic acid of formula (IV) with the guanidine (or derivative) of formula ($R'_1$—$NH_2$) is preferably carried out in a manner known per se in a protic or aprotic, but inert organic solvent. In this case solvents such as methanol, isopropanol, tert-butanol, dimethylformamide or tetrahydrofuran are used at temperatures ranging from 0° C. to the reflux temperature of these solvents, in particular during the reaction of the methyl or ethyl esters (X is a methoxy or an ethoxy) with the guanidines.

The reactions of the COX type compounds with the free guanidines are advantageously carried out in an inert aprotic solvent such as dimethylformamide, dichloromethane, tetrahydrofuran, dimethoxyethane, or dioxane, if appropriate by adding a base such as for example potassium tert-butoxide, sodium methoxide or an organic base such as N-methylmorpholine. However, water can also be used as solvent in the reactions of the compounds of formula (IV) with the guanidines of formula ($R'_1$—$NH_2$), for example by using a base such as sodium hydroxide.

If X is chlorine, the reaction will preferably be carried out by adding an acid trap, for example a base or of an excess of guanidine (or derivative). The reaction mixture is then treated and if desired the reaction product is purified according to the methods known to a person skilled in the art.

The protective groups optionally present in the compounds obtained from the compounds of formula (IV) and ($R'_1$—$NH_2$) are then eliminated by standard methods; for example, the tert-butyl ester groups are converted to carboxylic acid by treatment with trifluoroacetic acid, the benzyl groups are eliminated by hydrogenation or the fluorenylmethoxycarbonyl groups are also eliminated in the presence of secondary amine and other reactions are carried out using standard methods, for example acylation reactions. If necessary, the conversion into physiologically acceptable salts is carried out by methods known to a person skilled in the art.

The starting compounds of formula (II) or (IV) can be prepared according to the methods described in literature or are also accessible by analogy. The preparation of the compounds of formula (II) is illustrated in the diagram described below, it being understood that the present invention is not restricted to these syntheses or these starting products. It is not a major difficulty for a person skilled in the art to envisage modifications to the syntheses described in our Application for the preparation of other compounds of formula (II) according to the invention.

The compounds of formula (I) are compounds having a pharmacological activity and can therefore be used as medicaments in the treatment or the prevention of bone disease, tumorous diseases as well as cardiovascular disorders.

A subject of the present invention is therefore the compounds of formula (I) and/or their physiologically acceptable salts and/or their prodrugs as medicaments.

The compounds of formula (I) as well as their physiologically acceptable salts and their prodrugs can be administered to animals, preferably to mammals and in particular to human beings as therapeutic or prophylactic medicaments.

They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts and/or its prodrugs as active ingredient as well as current and pharmaceutically inert supports and/or additives.

The pharmaceutical compositions according to the invention allow enteral or parenteral administration which contain an effective dose of at least one compound of formula (I) and/or its physiologically acceptable salts and/or its prodrugs as active ingredient as well one or more pharmaceutically inert supports and/or usual additives.

A subject of the invention is therefore the pharmaceutical compositions containing a compound of formula (I) as defined previously as well as one or more excipients.

The medicaments can be administered orally, for example in the form of pills, tablets, coated tablets, film-encased tablets, granules, gelatin capsules and soft capsules, solutions, syrups, emulsion, suspension or aerosol mixture.

Administration can however be carried out by rectal route, for example in the form of suppositories or by parenteral route, for example in the form of injectable solutions or infusions, microcapsules or implants, or by percutaneous route, for example in the form of an ointment, solutions, pigments or colorants, by transdermal route in the form of patches or by other routes such as in the form of an aerosol or nasal spray.

The pharmaceutical compositions according to the invention are prepared according to methods known per se, organic or inorganic, pharmaceutically inert supports being added to the compounds of formula (I) and/or their physiologically acceptable salts and/or their prodrugs. For the production of pills, tablets, coated tablets and hard gelatin capsules, it is possible for example, to use lactose, corn starch or its derivatives, talc, stearic acid or its salts, etc. Suitable supports for soft gelatin capsules or suppositories are for example fats, waxes, semi-solid or liquid polyols, natural or modified oils etc. Appropriate vehicles for the preparation of solutions, for example injectable solutions, emulsions or syrups are for example water, alcohols, glycerol, polyols, sucrose, inverted sugars, glucose, vegetable oils, etc. Suitable supports for the microcapsules or the implants are for example glyoxilic acid and lactic acid copolymers. The pharmaceutical preparations normally contain 0.5% to 90% by weight of the compounds of formula (I) and/or their physiologically acceptable salts.

In addition to the active ingredients and the supports, the pharmaceutical preparations can contain additives such as for example diluting agents, disintegration agents, binding agents, lubricants, wetting agents, stabilisers, emulsifiers, preservatives, sweetening agents, coloring, flavouring or aromatizing agents, thickeners, buffering agents, and solvents or solubilizing agents or agents to obtain a delayed release effect and also salts to modify the osmotic pressure, coating agents or antioxidants.

They can also contain two or more compounds of formula (I) and/or their physiologically acceptable salts and/or their prodrugs. Moreover, in addition to at least one or more compounds of formula (I) and/or their physiologically acceptable salts and/or their prodrugs, they can contain at least one or more other active ingredients which can be used for therapeutic or prophylactic uses.

The pharmaceutical preparations (pharmaceutical compositions) normally contain 0.2 to 500 mg, and preferably 1 to 200 mg of the compound of formula (I) and/or their physiologically acceptable salts and/or their prodrugs.

The compounds of formula (I) are quite particularly antagonists of vitronectin receptors and are therefore capable for example of inhibiting the adhesion of osteoclasts on the surface of the bone and therefore bone resorption by the osteoclasts.

The action of the compounds of formula (I) can be demonstrated for example in a test in which the inhibition of the binding of vitronectin to the cells which contain the vitronectin receptor is determined. Further information about this test is given below. As antagonists of the vitronectin receptor, the compounds of formula (I) and their physiologically acceptable salts and their prodrugs are in general suitable for the treatment or prevention of diseases linked to the interactions between the vitronectin receptors and their ligands, in the process of cell-cell or cell-matrix interaction or which can be influenced by the inhibition of interactions of this type, to relieve or cure when an inhibition of interactions of this type is desired. As explained at the beginning, such an interaction plays an important role in bone resorption, in angiogenesis or in the proliferation of smooth vascular muscle cells.

Bone diseases in which the treatment or prevention require the use of the compounds of formula (I), are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments, by glucocorticoids, therapies linked to taking steroids or corticosteroids or by male or female sex hormone deficiencies.

All these disorders are characterized by bone loss, which is caused by a lack of equilibrium between bone formation and bone destruction and which can be favourably influenced by the inhibition of bone resorption by the osteoclasts. Besides this use as an inhibitor of bone resorption mediated via the osteoclasts, the compounds of formula (I) and their physiologically acceptable salts and their prodrugs are used as inhibitors of tumorous growth or cancerous metastases, in the treatment of inflammatory disorders, for the treatment or prevention of cardiovascular disorders, such as arteriosclerosis or the recurrence of stenosis, or the treatment or prevention of nephropathy or retinopathy such as for example diabetic retinopathy.

The compounds according to the invention can also have an activity vis-à-vis other integrins which interact with their ligand via the tripeptide sequence RGD ($\alpha_v\beta_1$, $\alpha_v\beta_5$, $\alpha_{IIb}\beta_3$), giving them properties which can be used pharmacologically to treat the pathologies associated with these receptors.

This activity vis-à-vis the integrins therefore makes the compounds of formula (I) of use in the prevention or treatment of numerous diseases such as those mentioned above or in Dermot Cox's review DN§P 8(4) May 1995, 197–205 the content of which is incorporated in the present Application.

A more particular subject of the invention is therefore a compound of formula (I) and/or its physiologically acceptable salts and/or its prodrugs as defined above as a medicament having an antagonist activity on the vitronectin receptor A more particular subject of the invention is therefore a compound of formula (I) and/or its physiologically acceptable salts and/or its prodrugs as defined above as a medicament having an inhibitory action on bone resorption or for the treatment or prevention of osteoporosis A more particular subject of the invention is therefore a compound of formula (I) and/or its physiologically acceptable salts and/or its prodrugs as defined above as a medicament having an inhibitory action on tumorous growth or cancerous metastases A more particular subject of the invention is therefore a compound of formula (I) and/or its physiologically acceptable salts and/or its prodrugs as defined above as a medicament having an an anti-inflammatory action or for the treatment or prevention of cardiovascular disorders, the recurrence of stenosis, arteriosclerosis, nephropathies or retinopathies A subject of the present invention is also the use of the compounds of formula (I) and/or their physiologically acceptable salts and/or their prodrugs as defined above for the preparation of medicaments intended for the prevention or the treatment of osteoporosis.

A subject of the present invention is also the use of the compounds of formula (I) and/or their physiologically acceptable salts and/or their prodrugs as defined above for the preparation of medicaments intended to inhibit tumorous growth or cancerous metastases.

A subject of the present invention is also the use of the compounds of formula (I) and/or their physiologically acceptable salts and/or their prodrugs as defined above for the preparation of medicaments intended for the prevention or treatment of cardiovascular disorders, the recurrence of stenosis, arteriosclerosis, nephropathies or retinopathies.

When the compounds of formula (I) are used, the doses can vary within wide limits and must be set according to the person treated. This depends for example on the compound used or the nature and severity of the disease to be treated and if the conditions are serious or chronic or if a prophylactic treatment is used.

In the case of administration by oral route, the daily dose in general varies from 0.01 to 100 mg/kg and preferably from 0.1 to 50 mg/kg, in particular from 0.1 to 5 mg/kg. For example for an adult weighing 75 kg a daily dose can be envisaged varying from 0.3 to 0.5 mg/kg.

In the case of administration by intravenous route, the daily dose varies approximately from 0.01 to 100 mg/kg and preferably from 0.05 to 10 mg/kg. The daily dose can be divided, in particular in the case of the administration of a large quantity of active ingredient, into several parts, for example 2, 3 or 4 parts. If appropriate, depending on individual behaviour, it may be necessary to administer different increasing or decreasing doses. Apart from the use of the compounds of formula (I) as medicaments, their use as a vehicle or support for active ingredients in order to deliver these active ingredients in a specific manner towards a target (Drug targeting, see Targeted Drug Delivery, R C Juliano, Handbook of Experimental Pharmacology, Vol 100, Ed. Born, G. V. R. et al, Springer Verlag). The active ingredients which can be delivered are in particular those used for the treatment or prevention of the diseases mentioned above.

The compounds of formula (I) and their salts can also be used as a diagnostic agent, for example for in vitro methods or as an auxiliary in biochemical studies in which blocking the vitronectin receptor or influencing the cell-cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrometry (MS), infrared (IR) and/or NMR spectrum. The compounds, which were purified by chromatography using an eluent which contains for example acetic or trifluoroacetic acid, and which are then dried or in which during the last stage of synthesis, for example trifluoroacetic acid was used to eliminate a tert-butyl protective group, sometimes contain, depending how the product was dried, the acid originating from the eluent or the last synthesis stage and therefore are found partially or completely in the form of the salt of the acid used, for example in the form of a salt of acetic or trifluoroacetic acid. They can also be more or less hydrated.

NMR analysis shows that the products of the present Application containing a cyclic acylguanidine group are mainly in the following form:

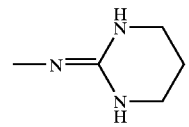

as compared with the form:

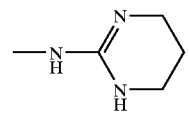

Chemical Abbreviations/names Optionally Used

AcOEt: ethyl acetate; EDCI: 1-(3-dimethylaminopropyl)-3-ethyl-carbodiimide hydrochloride; DMF: dimethylformamide; HOBt: 1-hydroxybenzotriazole hydrate; MeOH: methanol; TEA: triethylamine; TFA: trifluoroacetic acid; THF: tetrahydrofuran; MCPBA: metachloroperoxybenzoic acid; DBU: 1,8-diazabicyclo[5.4.0] undec-7-en; PTSA: paratoluenesulphonic acid; DPPA: diphenylphosphorylazide; DMSO: dimethylsulphoxide; Pd/C Palladium on carbon; Boc: terbutoxycarbonyl; CBz: benzyloxycarbonyl; DCC 1,3-dicyclohexylcarbodiimide; TMSBr: bromotrimethylsilane; TMSI: trimethylsilane iodide. IR: infrared; NMR: nuclear magnetic resonance; MS: mass spectrum; PES: positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography).

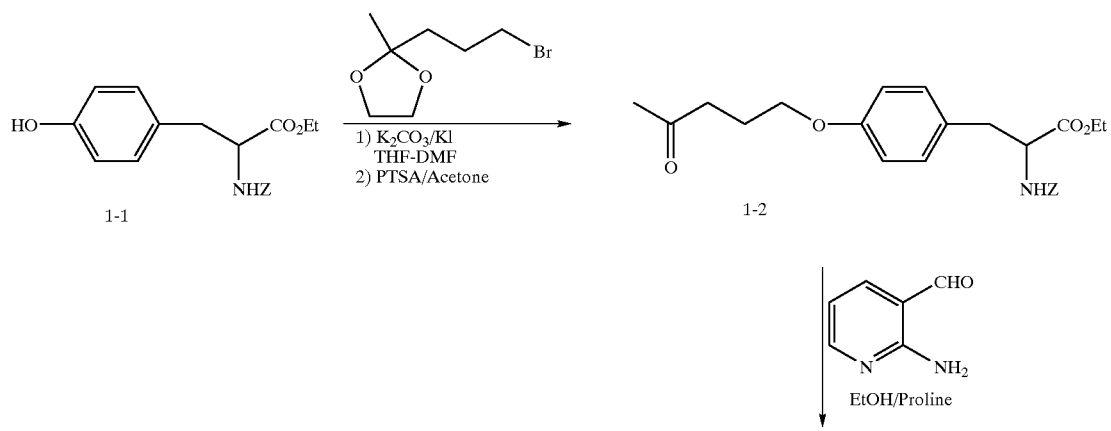

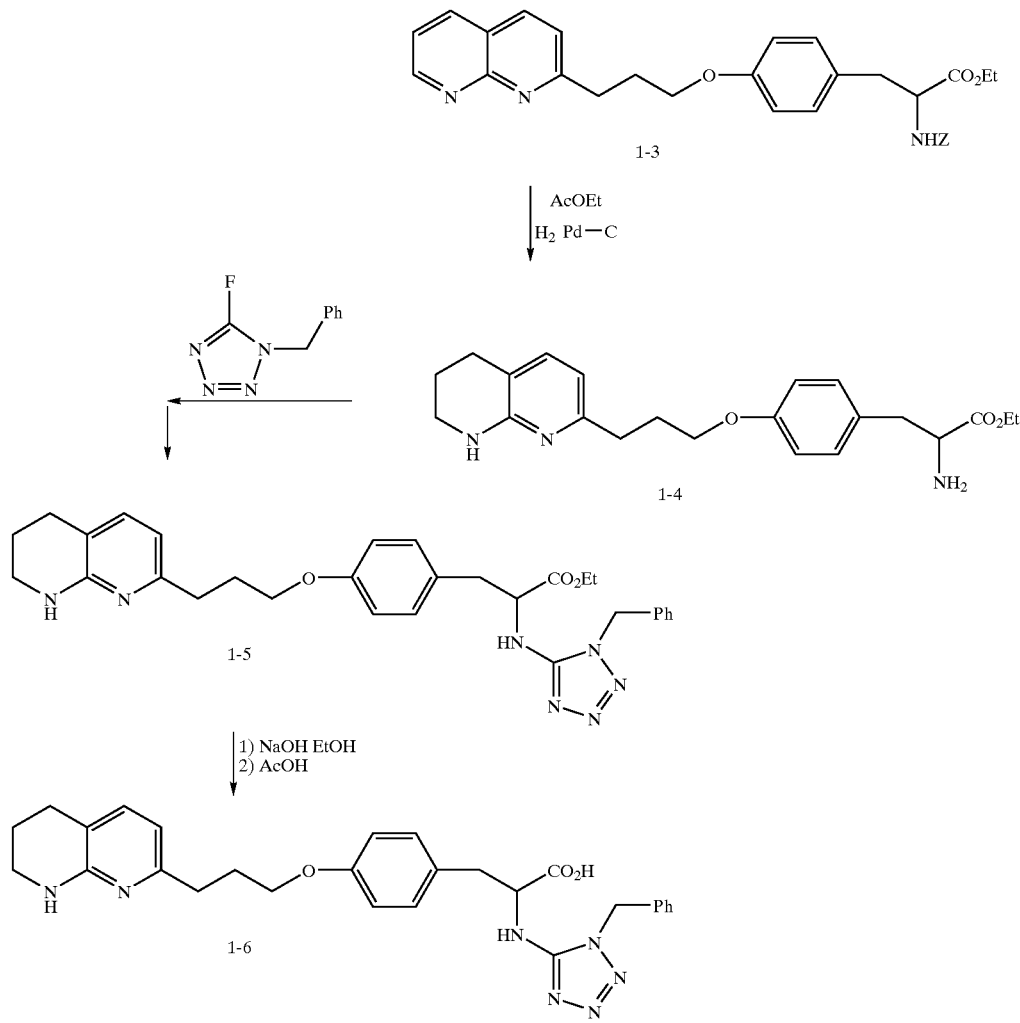

Example 1
N-[1-(phenylmethyl)-1H-tetrazol-5-yl]-O-[3-(5,6,7,8-tetrahydro-1,8-naphthyridin-2-yl)propyl]-L-tyrosine
Ethyl O-(4-oxopentyl)-N-[(phenylmethoxy)carbonyl]-L-tyrosinate (1-2)

A mixture constituted by ethyl N-Z-L-tyrosinate 1-1 (3 g, 9 mmoles), potassium carbonate (3 g), potassium iodide (catalytic quantity) and 2-(3-bromopropyl)-2-methyl-1,3-dioxolane (3.8 g; 18 mmoles) in 30 ml of THF and 30 ml of DMF is heated under reflux for 2 hours. After concentration under reduced pressure, the residue is taken up in an AcOEt/H$_2$O mixture followed by decanting and drying, and the organic phase is concentrated under reduced pressure. 3.8 g of crude product is obtained in the form of a ketal. 50 ml of acetone and 100 mg of PTSA are added to the crude product and the reaction medium is heated under reflux for one hour followed by evaporating under reduced pressure. The residue is taken up in a 1N H$_2$O/AcOEt/NaOH mixture followed by decanting, washing the organic phase with water, drying over MgSO4, filtering and concentrating under reduced pressure until 3.2 g of expected product is obtained 1-2.

IR (CHCl$_3$)
—NH 3436 cm$^{-1}$; C=O 1716 cm$^{-1}$; Aromatic+amide II 1612, 1580, 1512 cm$^{-1}$ Ethyl N-[(phenylmethoxy)carbonyl]-O-3-(1,8-naphthyridin-2-yl)propyl]-L-tyrosinate (1-3)

A mixture constituted by 1-2 (1.28 g 3 mmoles), 2-amino-3-pyridinecarboxaldehyde (366 mg) and L-proline (170 mg; 1.5 mmoles) in 100 ml of ethanol is heated under reflux for 4 hours then concentrated under reduced pressure until the crude product is obtained which is purified by chromatography eluting with a gradient of 50 to 100% of AcOEt in cyclohexane. 230 mg of 1-3 is obtained.

IR (CHCl$_3$)
—NH 3430 cm$^{-1}$; C=O 1720 cm$^{-1}$; Heterocycle+Aromatic+amide II 1610, 1582, 1558, 1512, 1500 cm$^{-1}$ Ethyl O-[3-(5,6,7,8-tetrahydro-1,8-naphthyridin-2-yl)propyl]-L-tyrosinate (1-4)

Naphthyridine 1-3 (920 mg) in ethyl acetate (80 ml) in the presence of Pd/C (400 mg) is hydrogenated under a pressure of 1.8 bar followed by agitating overnight. The reaction medium is filtered then evaporated under reduced pressure. 600 mg of the expected product 1-4 is obtained.

IR (CHCl₃)

—NH/NH$_2$ 3438, 3389 cm$^{-1}$; C=O 1730 cm$^{-1}$; Heterocycle+Aromatic 1658, 1611, 1599, 1587, 1512 cm$^{-1}$.

Ethyl N-[1-(phenylmethyl)-1H-tetrazol-5-yl]-O-[3-(5,6,7,8-tetrahydro-1,8-naphthyridin-2-yl)propyl]-L-tyrosinate (1-5)

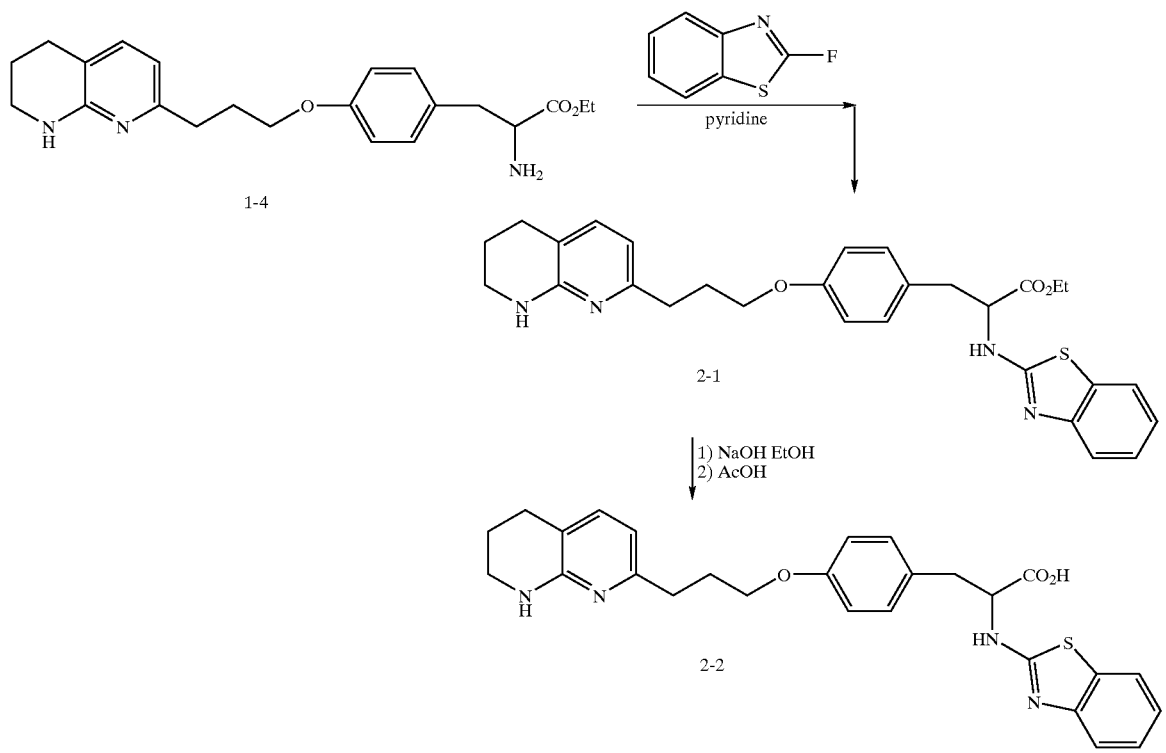

A mixture constituted by 1-4 (76 mg; 0.2 nmole), 5-fluoro-1-(phenylmethyl)-1H-tetrazole (36 mg) in 3 ml of pyridine is agitated for 3 hours, followed by evaporating under reduced pressure and purifying by chromatography eluting with a mixture constituted by cyclohexane/AcOEt (100/0→0/100). 115 mg of 1-5 is obtained.

IR (CHCl₃)

—NH 3440, 3396 cm$^{-1}$; C=O 1735 cm$^{-1}$; Heterocycle+Aromatic 1599, 1588, 1512, 1498 cm$^{-1}$.

N-[1-(phenylmethyl)-1H-tetrazol-5-yl]-O-[3-(5,6,7,8-tetrahydro-1,8-naphthyridin-2-yl)propyl]-L-tyrosin (1-6)

0.15 ml of 2N soda (0.3 mmole) is added to a solution of 1-5 (85 mg; 0.15 mmole) in 5 ml of ethanol followed by agitating for 3 hours at ambient temperature. Acetic acid is then added followed by evaporating under reduced pressure. The crude product is solubilized in a CH₂Cl₂/AcOEt mixture and poured into isopropyl ether. Crystallization is observed, then the solid is filtered in order to obtain 70 mg of the expected product 1-6.

Rf=0.10 (CH₂Cl₂/MeOH/NH₄OH 90/10/1)

M.p.=115° C.

IR (Nujol)

OH/NH region absorption; C=O 1667 cm$^{-1}$; Heterocycle+Aromatic 1605, 1508, 1493 cm$^{-1}$.

NMR (DMSO) 1.74 (m); 2.00 (m), 2.58 (t); 2.59 (t); 2.90 (dd, J=10–13.5); 3.13 (dd, J=4.5–13.5); 3.23 (m); 3.89 (t, J=6.5); 4.21 (m); 5.41 (J$_{AB}$=16.5); 6.27 (d, J=7); 6.32 (t, J=2.5); 6.73–7.11 (AA'BB'); 7.02 (d. J=7); 7.16 (m); 7.27 (m); 7.33; 12.99 (1).

MS

514Da=MH$^+$

Example 2

N-(2-benzothiazolyl)-O-[3-(5,6,7,8-tetrahydro-1,8-naphthyridin-2-yl)propyl]-L-tyrosine Ethyl N-(2-benzothiazolyl)-O-[3-(5,6,7,8-tetrahydro-1,8-naphthyridin-2-yl)propyl]-L-tyrosinate (2-1)

A mixture constituted by 1-4 (150 mg, 0.4 mmole) and 2-fluorobenzothiazole (75 mg; 0.5 mmole) in 3 ml of pyridine is agitated at ambient temperature then heated under reflux for minutes, followed by evaporating under reduced pressure and purifying by chromatography eluting with an AcOEt/CH₂Cl₂ mixture 50/50 in order to obtain 90 mg of the expected 2-1.

IR (Nujol)

OH/NH region absorption; C=O 1738 cm$^{-1}$; Conjugated system+Aromatic 1598, 1560, 1532, 1506 cm$^{-1}$.

N-(2-benzothiazolyl)-O-[3-(5,6,7,8-tetrahydro-1,8-naphthyridin-2-yl)propyl]-L-tyrosine (2-2)

The operation is carried out as for 1-6 but starting with 0.15 ml of 2N soda (0.3 mmole) and 80 mg of 2-1 (0.155 mmole) in 5 ml of ethanol. Rf=0.28 (CH₂Cl₂/MeOH/NH₄OH 90/10/1)

IR (Nujol)

OH/NH region absorption; C=O 1670 cm$^{-1}$; Heterocycle+Aromatic 1628, 1607, 1598, 1568, 1542, 1512 cm$^{-1}$.

NMR (DMSO) 1.73 (m); 1.96 (m); 2.54 (m); 2.58 (m); 2.93 (dd); 3.20 (masked); 3.22 (b); 3.87 (t); 4.13 (bq); 6.25

(d); 6.30 (b); 6.72 (d); 6.96 (t); 6.99 (d); 7.06 (d); 7.17 (t); 7.34 (d); 7.60 (d); 7.62 (d); 12.4 (spread).

N-(2-benzoxazolyl)-O-[3-(5,6,7,8-tetrahydro-1,8-naphthyridin-2-yl)propyl]-L-tyrosine (3-2)

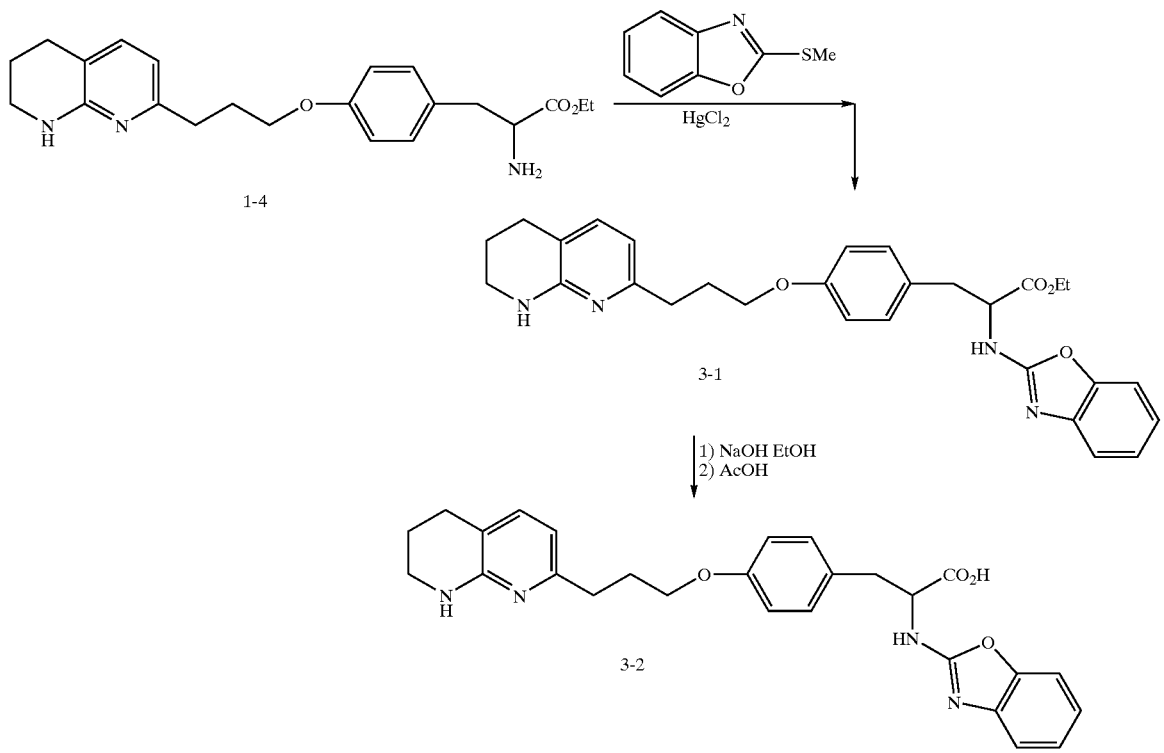

Example 3
N-(2-benzoxazolyl)-O-[3-(5,6,7,8-tetrahydro-1,8-naphthyridin-2-yl)propyl]-L-tyrosine
Ethyl N-(2-benzoxazolyl)-O-[3-(5,6,7,8-tetrahydro-1,8-naphthyridin-2-yl)propyl]-L-tyrosinate (3-1)

A mixture constituted by 1-4 (120 mg, 0.3 mmole) and 2-methylthiobenzoxazole (0.5 ml) and 30 mg of mercury dichloride is heated at 140° C. for 3 hours, followed by evaporating under reduced pressure and purifying by chromatography eluting with a gradient of AcOEt (0→100) in $CH_2Cl_2$ in order to obtain 55 mg of the expected 3-1.

IR ($CHCl_3$)

NH 3424 cm$^{-1}$ (Max); C=O 1735 cm$^{-1}$; conjugated system+Aromatic 1644, 1599, 1583, 1512 cm$^{-1}$.

The operation is carried out as for 1-6 but with 2 ml of 2N soda (0.2 mmole) and 45 mg of 3-1 (0.09 mmole) in 8 ml of ethanol.

Rf=0.33 ($CH_2Cl_2$/MeOH/$NH_4OH$ 90/10/1)

IR (Nujol)

OH/NH region absorption 3422 cm$^{-1}$; C=O 1700, 1672 cm$^{-1}$; C=O and C=N 1642 cm$^{-1}$; Conjugated system+Aromatic 1581, 1561, 1508, cm$^{-1}$.

NMR (DMSO) 1.73 (m); 1.96 (m); 2.55 (m); 2.58 (m); 2.95 (dd); 3.19 (m); 3.21 (dd); 3.86 (t); 3.94 (m); 6.30 (b); 6.25 (d); 7.01 (d); 6.70 (d)-7.04 (d); 7.06; 6.92 (t)-7.07 (masked)-7.20 (d)-7.27 (d).

MS 473$^+$=[M+H]$^+$

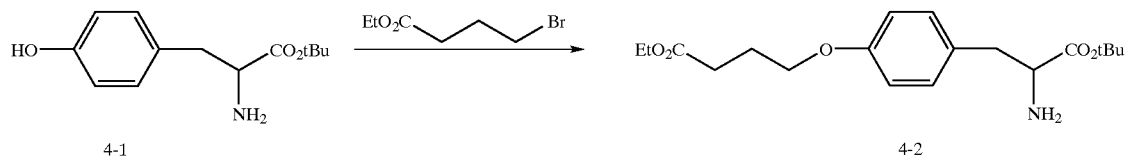

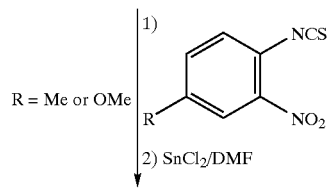

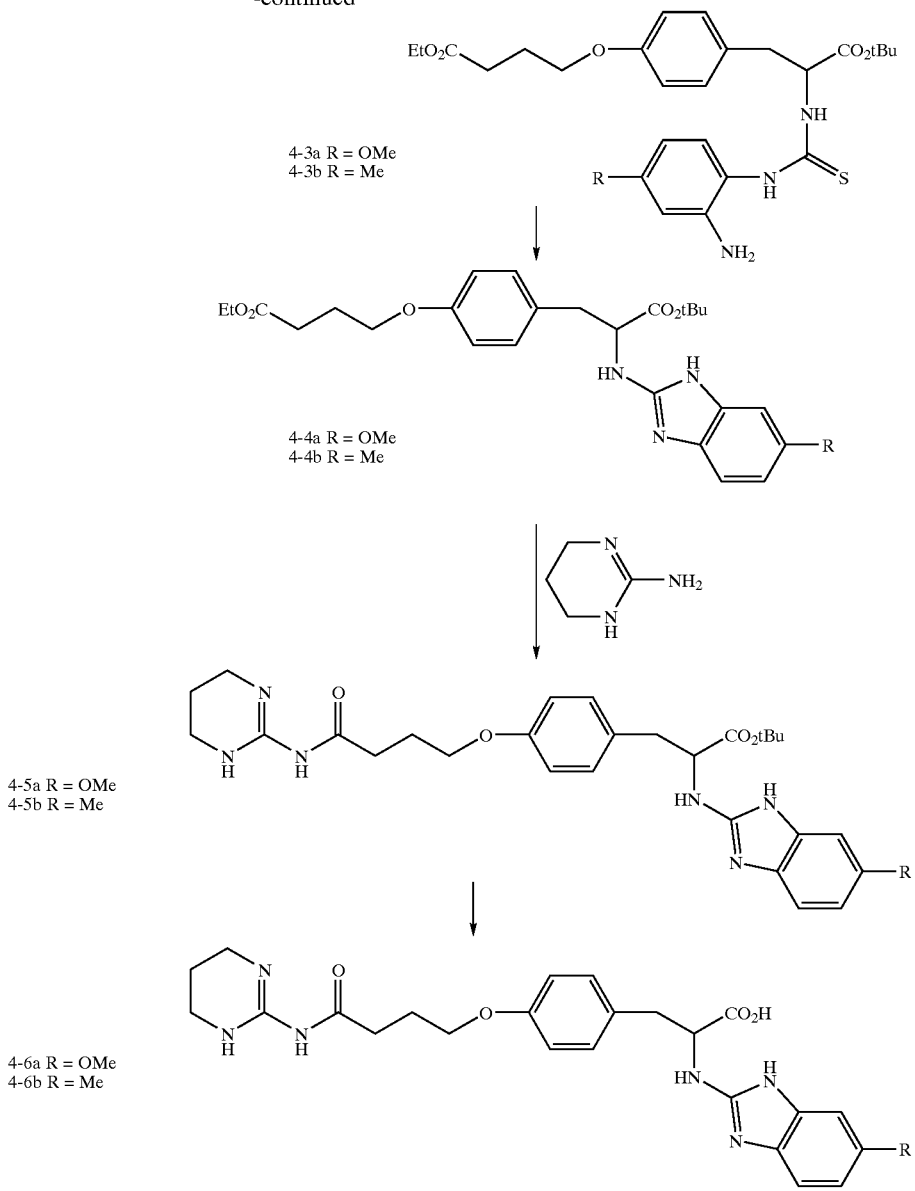

4-3a R = OMe
4-3b R = Me 4-4a R = OMe
4-4b R = Me 4-5a R = OMe
4-5b R = Me 4-6a R = OMe
4-6b R = Me

Example 4a

N-[[5-methoxy-1H-benzimidazol-2-yl]-O-[4-oxo-4-[(1,4,5,6-tetrahydro-2-pyrimidinyl)amino]butyl]-L-tyrosine (1,1-dimethyl ethyl) O-(4-ethoxy-4-oxobutyl)-L-tyrosinate (4-2)

Potassium tertbutylate (3.36 g, 30 mmoles) is added to a solution of tyrosine 4-1 (5 g, 21 mmoles) in 100 ml of DMF, followed by agitating for 30 minutes while cooling down in a water+ice bath, then the bromoester (ethyl 4-bromobutanoate) (3.6 ml, 25 mmoles) in solution in 10 ml of DMF is added. The reaction medium is agitated overnight at ambient temperature, followed by evaporating under reduced pressure, taking up the dry extract in a water/ethyl acetate mixture, decanting, drying the organic phase, filtering, evaporating then purifying by chromatography eluting with a Heptane/ethyl acetate gradient (100/0→0/100). 5.2 g of the expected product 4-2 is obtained.

IR (CHCl$_3$)

NH$_2$: 3384 cm$^{-1}$; C=O 1727 cm$^{-1}$; Aromatic 1612, 1582, 1512 cm$^{-1}$.

(1,1-dimethyl ethyl) N-[[(2-amino-4-methoxyphenyl)amino]thioxomethyl]-O-(4-ethoxy-4-oxobutyl)-L-tyrosinate (4-3a)

The aminoester 4-2 (350 mg, 1 mmole) in 20 ml of THF is mixed with 4-methoxy-2-nitrophenyl isothiocyanate (210 mg, 1 mmole), followed by agitating for 1 hour at ambient temperature, evaporating under reduced pressure, then adding SnCl$_2$ (380 mg then 190 mg, 3 mmoles) in 10 ml of DMF and agitating for 4 hours at ambient temperature. After evaporating under reduced pressure and taking up in a water/NaHCO$_3$/AcOEt mixture, decanting, drying the organic phase and evaporating under reduced pressure, 530 mg of crude product is obtained.

(1,1-dimethyl ethyl) O-(4-ethoxy-4-oxobutyl)-N-[5-methoxy-1H-benzimidazol-2-yl]-L-tyrosinate (4-4a)

500 mg of HgCl$_2$ is added to the amino thiourea 4-3a (530 mg, 1 mmole) in 30 ml of DMF and 3 ml of TEA, followed by agitating for 2 hours at ambient temperature, evaporating under reduced pressure and taking up in a water/NaHCO$_3$/AcOEt mixture. The organic phase is decanted, dried and evaporated to dryness under reduced pressure. The residue is chromatographed eluting with a gradient of heptane/AcOEt (100/0→50/50). 430 mg of crude product 4-4a is obtained.

IR (CHCl$_3$)

C=O 1727 cm$^{-1}$; Conjugated system+Aromatic 1658, 1610, 1596, 1513, 1491 cm$^{-1}$.

(1,1-dimethyl ethyl) N-[5-methoxy-1H-benzimidazol-2-yl]-O-[4-oxo-4-[(1,4,5,6-tetrahydro-2-pyrimidinyl)amino]butyl]-L-tyrosinate (4-5a)

100 mg of 2-amino-1,4,5,6-tetrahydropyrimidine is added to a solution of the ester 4-4a (100 mg) in 7 ml of CH$_2$Cl$_2$, followed by agitating for 3 hours at ambient temperature, evaporating under reduced pressure then purifying by chromatography elating with a CH$_2$Cl$_2$/MeOH/water/AcOH mixture 90/10/1/1. 29 mg of the expected 4-5a is obtained.

IR (CHCl$_3$)

OH/NH region absorption; C=O 1730, 1712 cm$^{-1}$; C=O C=N 1687, 1664 cm$^{-1}$; Conjugated system+Aromatic 1638, 1612, 1603, 1578, 1539, 1511 cm$^{-1}$ N-[5-methoxy-1H-benzimidazol-2-yl]-O-[4-oxo-4-[(1,4,5,6-tetrahydro-2-pyrimidinyl)amino]butyl]-L-tyrosine (4-6a)

2 ml of trifluoroacetic acid is added to 25 mg of ester 4-5a in 5 ml of dichloromethane, followed by agitating for 3 hours at ambient temperature then adding toluene. After evaporating under reduced pressure, taking up in dichloromethane and crystallizing by adding an Et$_2$O/pentane mixture, 11 mg of 4-6a is obtained.

Rf=0.35 (CH$_2$Cl$_2$/MeOH/AcOH/water 90/10/1/1)

NMR (DMSO) 1.84 (m) CH$_2$; 1.96 (m) CH$_2$; 2.52 (masked) CH$_2$; 2.95 (m) 3.15 (m) CH$_2$ AB; 3.34 (bs) 2×CH$_2$; 3.72 (s) OCH$_3$; 3.94 (m) CH$_2$; 4.48 (m) CH; 6.82–7.16 AA'BB'; 6.59 (m)-6.80 (masked)-7.09 aromatic H; 9.04–8.95–11.60 the NH's.

MS 495$^+$=M+H$^+$

Example 4b
N-[5-methyl-1H-benzimidazol-2-yl]-O-[4-oxo-4-[(1,4,5,6-tetrahydro-2-pyrimidinyl)amino]butyl]-L-tyrosine (1,1-dimethyl ethyl) N-[[(2-amino-4-methylphenyl)amino]thioxomethyl]-O-(4-ethoxy-4-oxobutyl)-L-tyrosinate (4-3b)

The aminoester 4-2 (351 mg, 1 mmole) in 20 ml of THF is mixed with 4-methyl-2-nitrophenyl isothiocyanate (194 mg), followed by agitating for 1 hour at ambient temperature, evaporating under reduced pressure, then adding SnCl$_2$ (380 mg then 190 mg, 3 mmoles) in 10 ml of DMF and agitating for 2 hours at ambient temperature. The reaction medium is then evaporated under reduced pressure followed by taking up in a water/NaHCO$_3$/AcOEt mixture, decanting, drying the organic phase then evaporating to dryness under reduced pressure. 550 mg of crude product is obtained.

IR (CHCl$_3$)

Complex NH 3280 cm$^{-1}$, C=O 1727 cm$^{-1}$; Conjugated system+Aromatic 1632, 1610, 1593, 1571, 1513 cm$^{-1}$.

(1,1-dimethyl ethyl) O-(4-ethoxy-4-oxobutyl)-N-[5-methyl-1H-benzimidazol-2-yl]-L-tyrosinate (4-4b)

70 mg of HgCl$_2$ is added to the amino thiourea 4-3b (55 mg) in 5 ml of DMF and 0.5 ml of TEA, followed by agitating for 2 hours at ambient temperature, evaporating under reduced pressure and taking up in a water/NaHCO$_3$/AcOEt mixture, decanting, drying the organic phase over Na$_2$SO$_4$ and evaporating to dryness under reduced pressure. 45 mg of crude product 4-4b is obtained.

IR (CHCl$_3$)

Complex NH 3280 cm$^{-1}$, C=O 1727 cm$^{-1}$; Conjugated system+heterocycle+Aromatic 1671, 1638, 1594, 1513, 1491 cm$^{-1}$.

(1,1-dimethyl ethyl) N-[5-methyl-1H-benzimidazol-2-yl]-O-[4-oxo-4-[(1,4,5,6-tetrahydro-2-pyrimidinyl)amino]butyl]-L-tyrosinate (4-5b)

45 mg of 2-amino-1,4,5,6-tetrahydropyrimidine is added to a solution of the ester 4-4b (45 mg) in 5 ml of CH$_2$Cl$_2$, followed by agitating for 4 hours at ambient temperature, evaporating under reduced pressure then purifying by chromatography eluting with a CH$_2$Cl$_2$/MeOH mixture 90/10. 23 mg of the expected 4-5b is obtained.

IR (CHCl$_3$)

Complex NH 3250 cm$^{-1}$; C=O 1729, 1713 cm$^{-1}$; C=O C=N 1687, 1660, 1637 cm$^{-1}$; Conjugated system+Aromatic 1611, 1599, 1575, 1539, 1512 cm$^{-1}$.

N-[5-methyl-1H-benzimidazol-2-yl]-O-[4-oxo-4-[(1,4,5,6-tetrahydro-2-pyrimidinyl)amino]butyl]-L-tyrosine (4-6b)

1 ml of trifluoroacetic acid is added to 20 mg of the ester 4-5b in 3 ml of dichloromethane, followed by agitating for 5 hours at ambient temperature then adding toluene. After evaporating under reduced pressure, taking up in dichloromethane and crystallizing by adding an Et$_2$O/pentane mixture, 15 mg of 4-6b is obtained.

Rf=0.30 (CH$_2$Cl$_2$/MeOH/AcOH/water 90/10/1/1)

NMR (DMSO) 1.84 (m) CH$_2$; 3.34 (bs) 2×CH$_2$; 1.95 (quint) CH$_2$; 2.52 (masked) CH$_2$; 3.93 (t) CH$_2$; 2.34 (s) Ph-CH$_3$; 3.20 (dd) 2.98 (dd) Ph-CH$_2$; 4.53 (m) CH; 6.81–7.17 AA'BB'; 7.09 (s)-6.92 (m)-7.17 (masked) aromatic H; 9.11 (bs) NH of the ring in position 6; 11.72 2HNH.

MS 479$^+$=[M+H]$^+$

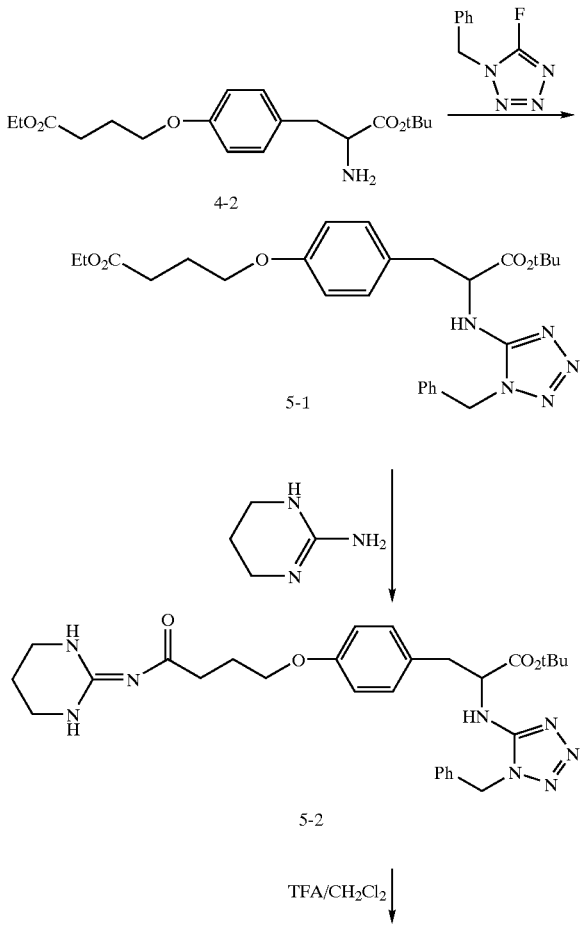

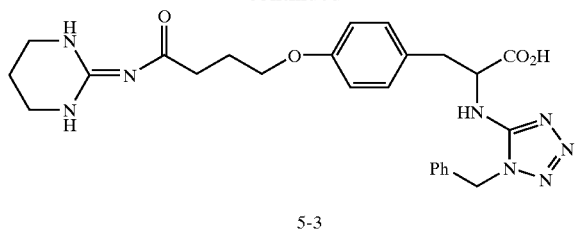

5-3

Example 5
O-[4-oxo-4-[(1,4,5,6-tetrahydro-2-pyrimidinyl)amino]butyl]-N-[1-(phenylmethyl)-1H-tetrazol-5-yl]-L-tyrosine (1,1-dimethyl ethyl) O-(4-ethoxy-4-oxobutyl)-N-[1-(phenylmethyl)-1H-tetrazol-5-yl]-L-tyrosinate (5-1).

A solution of aminoester 4-2 (325 mg, 0.92 mmole) and 5-fluoro-1-(phenylmethyl)-1H-tetrazole (170 mg, 0.95 mmole) in 15 ml of pyridine is heated at 100° C. for 2 hours. Evaporation is then carried out under reduced pressure until a dry extract is obtained which is purified by chromatography eluting with a heptane/AcOEt mixture 50/50. 270 mg of the expected product 5-1 is obtained.

IR (CHCl$_3$)

NH 3394 cm$^{-1}$; C=O 1728 cm$^{-1}$; Heterocycle+Aromatic 1603, 1512, 1498 cm$^{-1}$ (1,1-dimethyl ethyl) O-[4-oxo-4-[(1,4,5,6-tetrahydro-2-pyrimidinyl)amino]butyl]-N-[1-(phenylmethyl)-1H-tetrazol-5-yl]-L-tyrosinate (5-2)

The ester 5-1 (150 mg) is mixed with 2-amino-1,4,5,6-tetrahydropyrimidine (42 mg) in 5 ml of CH$_2$Cl$_2$ and agitation is carried out at ambient temperature for 24 hours. Evaporation is then carried out under reduced pressure and the dry extract obtained is purified by chromatography, eluting with a CH$_2$Cl$_2$/MeOH/water/AcOH mixture 90/10/1/1. 40 mg of the expected product 5-2 is obtained.

IR (CHCl$_3$)

OH/NH region complex absorption; C=O 1711, 1691 cm$^{-1}$; C=O+C=N 1663 cm$^{-1}$ Conjugated system+ Heterocycle+Aromatic 1602, 1512, 1498 cm$^{-1}$ O-[4-oxo-4-[(1,4,5,6-tetrahydro-2-pyrimidinyl)amino]butyl]-N-[1-(phenylmethyl)-1H-tetrazol-5-yl]-L-tyrosine (5-3)

2 ml of trifluoroacetic acid is added to 135 mg of ester 5-2 in 5 ml of dichloromethane, followed by agitating for 3 hours at ambient temperature, adding 10 ml of toluene, evaporating under reduced pressure, taking up in dichloromethane and crystallizing by adding an Et$_2$O/pentane mixture. 92 mg of 5-3 is obtained.

Rf=0.40 (CH$_2$Cl$_2$/MeOH/AcOH/water 90/10/1/1)

M.p.=195° C.

IR (Nujol)

OH/NH absorption, complex CO 1717 cm$^{-1}$; C=O+C=N 1696, 1675 cm$^{-1}$; Conjugated system+aromatic+Amide II: 1595, 1555, 1515, 1496 cm$^{-1}$.

NMR (DMSO) 2.56 (t) CH$_2$—CO; 1.99(m) CH$_2$; 3.95 (t) CH$_2$—O-Ph; 3.35 (masked) NH—CH$_2$-1.85 (m); 2.92 (dd) 3.12 (dd) Ph-CH$_2$; 4.29 CH—NH; 7.53 (d) CH—NH; 5.44 (AB) NCH$_2$-Ph; 6.77 7.17 -Ph-O; 7.17 2H 7.30 3H aromatic H; 8.87–11.4–12.9 mobile H's.

MS 507$^+$=[M+H]$^+$

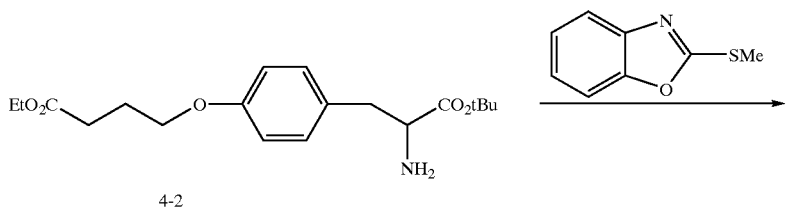

4-2

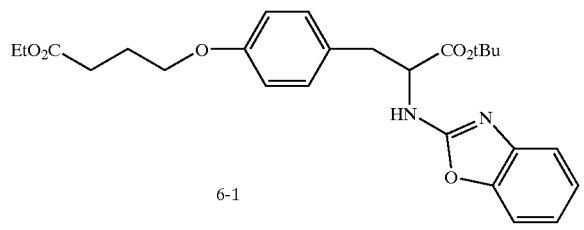

6-1

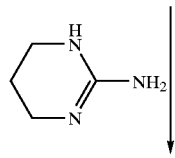

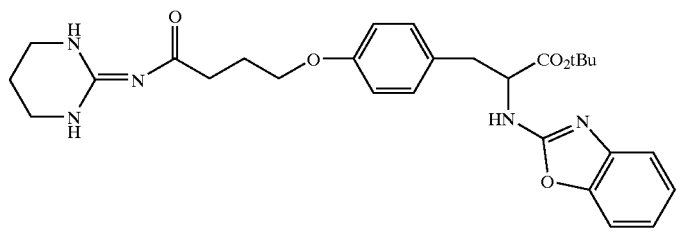

6-2

TFA/CH₂Cl₂ ↓

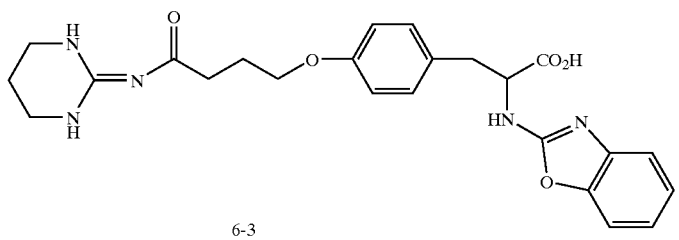

6-3

Example 6
N-(2-benzoxazolyl)-O-[4-oxo-4-[(1,4,5,6-tetrahydro-2-pyrimidinyl)amino]butyl]-L-tyrosine (1,1-dimethyl ethyl) N-(2-benzoxazolyl)-O-(4-ethoxy-4-oxobutyl)-L-tyrosinate (6-1)

A mixture constituted by aminoester 5-3 (1.05 g, 3 mmole), 2-methylthiobenzoxazole (660 mg, 4 mmoles) and HgCl₂ (50 mg) is heated at 140° C. for 4 hours. The mixture obtained after cooling down is purified by chromatography eluting with a heptane/AcOEt mixture 50/50. 370 mg of the expected product 6-1 is obtained.

IR (CHCl₃)

NH 3413 cm⁻¹; C=O 1729 cm⁻¹; Heterocycle+Aromatic 1642, 1612, 1582, 1512 cm⁻¹

(1,1-dimethyl ethyl) N-(2-benzoxazolyl)-O-[4-oxo-4-[(1,4,5,6-tetrahydro-2-pyrimidinyl)amino]butyl]-L-tyrosinate (6-2)

The ester 6-1 (370 mg) is mixed with 2-amino-1,4,5,6-tetrahydropyrimidine (200 mg) in 5 ml of CH₂Cl₂ and agitation is carried out at ambient temperature for 6 hours. The reaction medium is then evaporated under reduced pressure and the dry extract obtained is purified by chromatography eluting with a CH₂Cl₂/MeOH/water/AcOH mixture 90/10/1/1. 200 mg of the expected product 6-2 is obtained.

N-(2-benzoxazolyl)-O-[4-oxo-4-[(1,4,5,6-tetrahydro-2-pyrimidinyl)amino]butyl]-L-tyrosine (6-3)

3 ml of trifluoroacetic acid is added to 200 mg of ester 6-2 in 10 ml of dichloromethane, agitation is carried out for 2 hours at ambient temperature then 10 ml of toluene is added. After evaporating under reduced pressure, taking up in dichloromethane and crystallizing by adding an Et₂O/pentane mixture, 175 mg of 6-3 is obtained.

Rf=0.40 (CH₂Cl₂/MeOH/AcOH/water 90/10/1/1)

M.p.=115° C. (decomp.)

IR (Nujol)

OH/NH absorption; C=O 1695; C=O+C=N, 1671 cm⁻¹; heterocycle+aromatic: 1647, 1612, 1583, 1569, 1512 cm⁻¹.

NMR (DMSO) 1.84 (m) CH₂; 1.96 CH₂; 2.52 (masked) CH₂—CO; 2.91 (dd) 3.14 (dd) Ph-CH₂; 3.30 (m) NH—CH₂; 3.94 (t) CH₂—O-Ph; 4.36 (dt) CH—NH; 6.82 7.22 -Ph-O; 6.98 (dt) 1H 7.10 (dt) 1H 7.22 1H 7.33 (bd) 1H aromatic H; 8.33 (d) CH—NH; 8.88 (s) 11.45–12.80 mobile H's.

MS 466⁺=[M+H]⁺

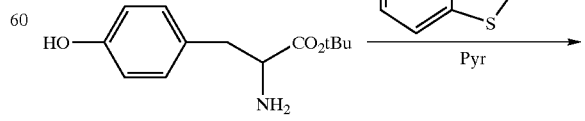

4-1

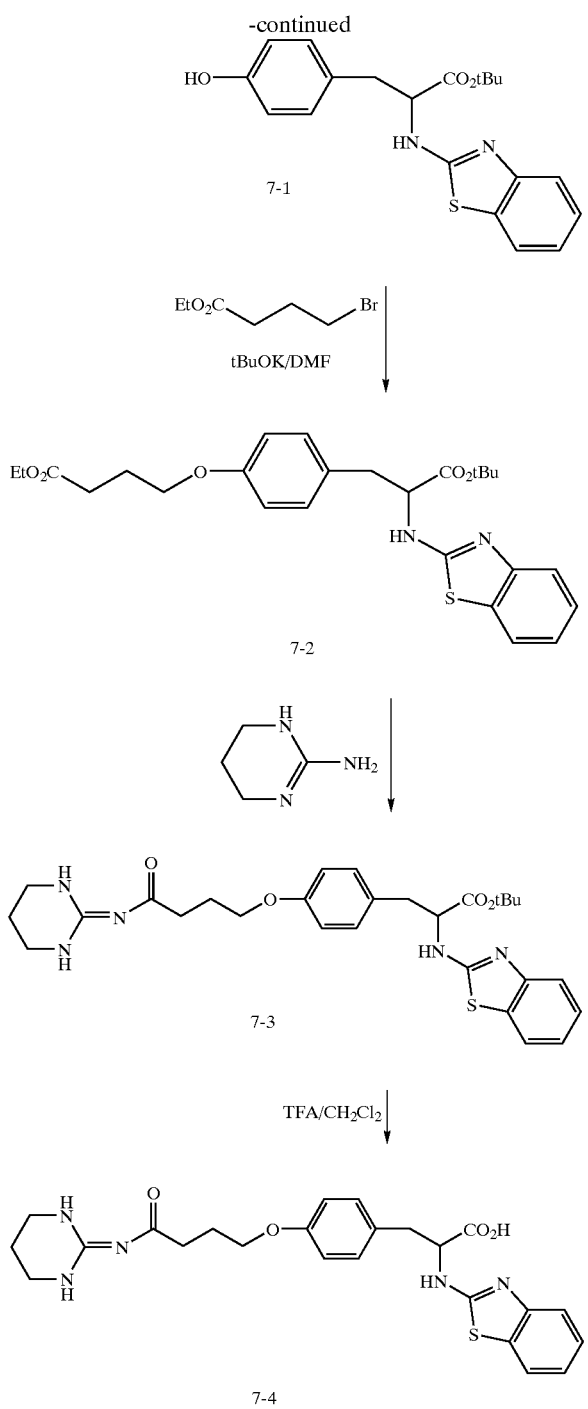

ethyl acetate mixture (100/0→0/100). 115 mg of expected product is obtained.

IR (CHCl$_3$)

—OH 3600 cm$^{-1}$; —NH 3414 cm$^{-1}$; C=O 1728 cm$^{-1}$; Conjugated system+aromatic+heterocycle: 1614, 1599, 1544 and 1515 cm$^{-1}$.

(1,1-dimethyl ethyl) N-(2-benzothiazolyl)-O-(4-ethoxy-4-oxobutyl)-L-tyrosinate (7-2)

30 mg of tBuOK then 44 μl of ethyl 4-bromobutanoate (0.3 mmole) are added to phenol 7-1 (90 mg, 0.24 mmole) in 3 ml of DMF, and agitation is carried out for 5 hours at ambient temperature. The solvent is then evaporated off, the dry extract is taken up in a water/AcOEt/NH$_4$Cl mixture followed by decanting, drying the organic phase, evaporating under reduced pressure and purifying by chromatography eluting with a heptane/AcOEt mixture (100/0→50/50). 90 mg of the expected 7-2 is obtained.

IR (CHCl$_3$)

—NH 3410 cm$^{-1}$; C=O 1728 cm$^{-1;}$ Conjugated system+aromatic+heterocycle: 1612, 1599, 1584, 1564, 1542 and 1512 cm$^{-1}$ (1,1-dimethyl ethyl) N-(2-benzothiazolyl)-O-(4-oxo-4-[(1,4,5,6-tetrahydro-2-pyrimidinyl)amino]butyl]-L-tyrosinate (7-3)

The ester 7-2 (80 mg) is mixed with 2-amino-1,4,5,6-tetrahydropyrimidine (40 mg) in 5 ml of CH$_2$Cl$_2$ and agitation is carried out at ambient temperature for 24 hours. After evaporating under reduced pressure, purifying the dry extract obtained by chromatography eluting with a CH$_2$Cl$_2$/MeOH mixture (100/0→90/10), 25 mg of the expected product 7-3 is obtained.

IR (CHCl$_3$)

NH 3420 cm$^{-1}$; C=O 1725; C=O+C=N: 1687 cm$^{-1}$; Conjugated system+Heterocycle+Aromatic 1638, 1599, 1565, 1542, 1512 cm$^{-1}$.

N-(2-benzothiazolyl)-O-[4-oxo-4-[(1,4,5,6-tetrahydro-2-pyrimidinyl)amino]butyl]-L-tyrosine (7-4)

2 ml of trifluoroacetic acid is added to 25 mg of ester 7-3 in 5 ml of dichloromethane, agitation is carried out for 2 hours at ambient temperature then 10 ml of toluene is added. After evaporating under reduced pressure, taking up in dichloromethane and crystallizing by adding an Et$_2$O/pentane mixture. 20 mg of 7-4 is obtained.

Rf=0.40 (CH$_2$Cl$_2$/MeOH/AcOH/water 90/10/1/1)

IR (CHCl$_3$)

OH/NH absorption; C=O 1695, 1668 cm$^{-1}$; Conjugated system+aromatic+Amide II: 1612, 1587, 1561, 1543, 1513 cm$^{-1}$ NMR (DMSO) 2.55 (masked) CH$_2$—CO; 1.98 CH$_2$; 3.95 CH$_2$—O-Ph; 3.35 (m) CH$_2$-1.85 (m) CH—CH$_2$, 2.91 3.13 Ph-CH$_2$; 4.58 (m) CH—NH; 8.40 (d) CH—NH; 6.83 7.21 -Ph-O; 7.02 (bt) 7.21 7.36 (bd) 7.65 (bd) aromatic H; 8.80 12.8 mobile H's.

MS 482$^+$=[M+H]$^+$

Example 7
N-(2-benzothiazolyl)-O-[4-oxo-4-[(1,4,5,6-tetrahydro-2-pyrimidinyl)amino]butyl]-L-tyrosine
(1,1-dimethyl ethyl) N-(2-benzothiazolyl)-L-tyrosinate (7-1)

A mixture constituted by (1,1-dimethyl ethyl) L-tyrosinate 4-1 (120 mg, 0.5 mmole) and fluorobenzothiazole (75 mg; 0.5 mmole) in 3 ml of pyridine is heated under reflux for 2 hours. The reaction medium is then evaporated under reduced pressure until a dry extracted is obtained which is purified by chromatography eluting with a heptane/

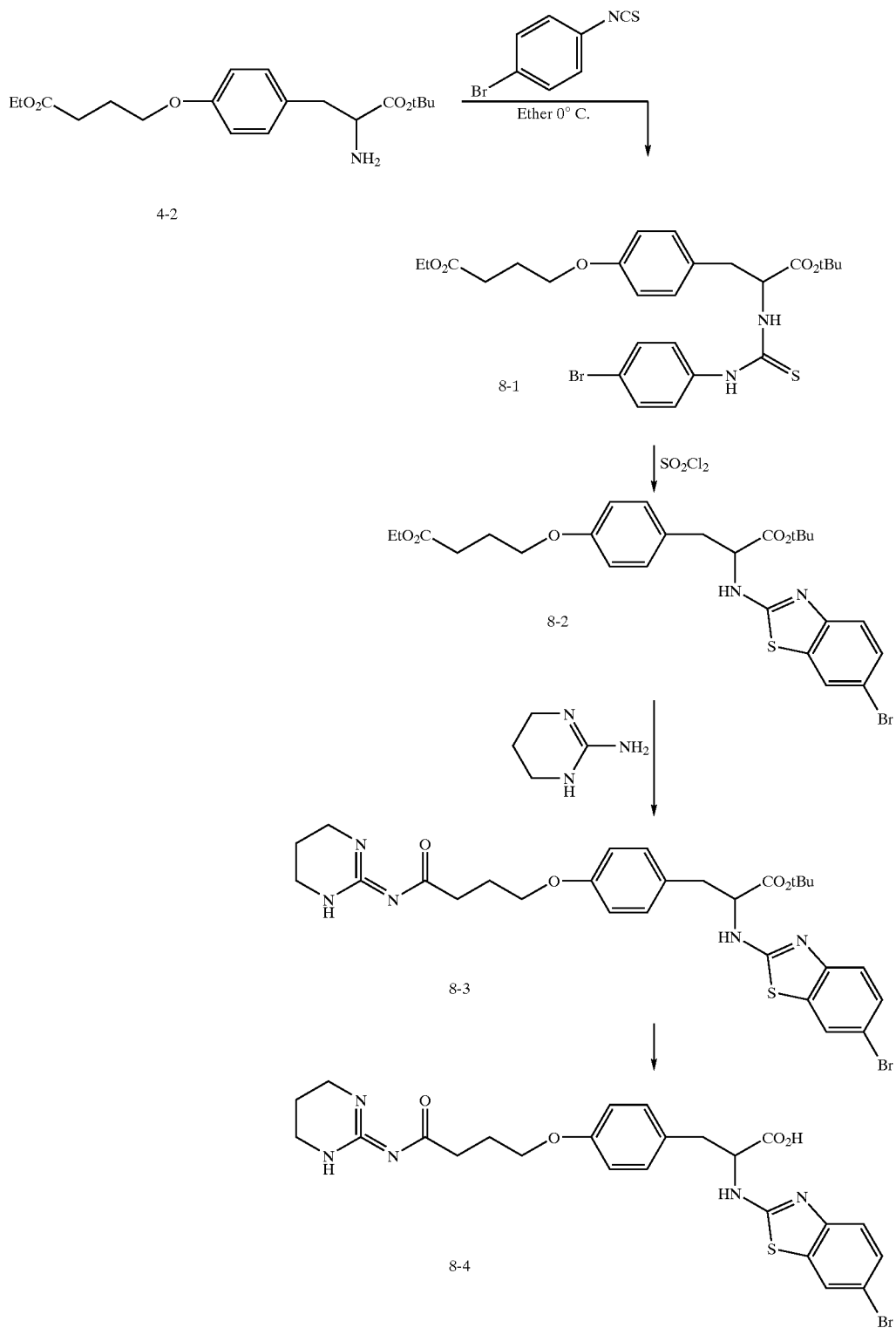

Example 8
N-(6-bromo-2-benzothiazolyl)-O-[4-oxo-4-[(1,4,5,6-tetrahydro-2-pyrimidinyl)amino]butyl]-L-tyrosine (1,1-dimethyl ethyl) N-[[(4-bromophenyl)amino]thioxomethyl]-O-(4-ethoxy-4-oxo-butyl)-L-tyrosinate (8-1)

4-bromophenyl isothiocyanate (1.61 g, 7.5 mmole) is added at approximately 0° C. to a solution of aminoester 4-2 (2.34 g, 6.6 mmole) in 50 ml of ether and agitation is carried out for two hours at ambient temperature, evaporation is carried out under reduced pressure, until a dry extract is obtained (4.03 g) corresponding to the expected thiourea.

MS
565$^+$/..=[M+H]$^+$
587$^+$/..=[M+Na]$^+$ (1,1-dimethyl ethyl) N-[6-bromo-2-benzothiazolyl]-O-(4-ethoxy-4-oxo-butyl)-L-tyrosinate (8-2)

0.6 ml of $SO_2Cl_2$ in 5 ml of chlorobenzene is added to a solution of amino thiourea 8-1 (3 g, 5.3 mmol) in 60 ml of chlorobenzene at 0° C., agitation is carried out for 2 hours at ambient temperature, followed by diluting in ethyl acetate, washing, drying and evaporating the organic phase under reduced pressure, in order to obtain the crude product which is purified by chromatography eluting with a heptane/ethyl acetate mixture 80/20. 593 mg of expected product is obtained 8-2.

MS
563$^+$/..=[M+H]$^+$
507$^+$/..=MH$^+$/..-tBu (1,1-dimethyl ethyl) N-(6-bromo-2-benzothiazolyl)-O-[4-oxo-4-[(1,4,5,6-tetrahydro-2-pyrimidinyl)amino]butyl]-L-tyrosinate (8-3)

80 mg of 2-amino-1,4,5,6-tetrahydropyrimidine is added to a solution of the ester 8-2 (123 mg) in 3 ml of THF, agitation is carried out for 20 hours at ambient temperature, 48 mg of tetrahydroaminopyrimidine is also added and agitation is carried out for 5 hours. After evaporating under reduced pressure, the mixture is chromatographed eluting with a $CH_2Cl_2$/AcOEt 80/20 then $CH_2Cl_2$/MeOH 90/10 mixture. 68 mg of the expected 8-3 is obtained.

MS
616$^+$/..=[M+H]$^+$/...
560$^+$/..=MH$^+$/..-tBu

N-(6-bromo-2-benzothiazolyl)-O-[4-oxo-4-[(1,4,5,6-tetrahydro-2-pyrimidinyl)amino]butyl]-L-tyrosine (8-4)

Hydrolysis of the ester is carried out as in the previous examples, but starting from 50 mg of 8-3 and twice 0.5 ml of TFA in 1.5 ml dichloromethane. 62 mg of 8-4 is obtained (in the form of the trifluoroacetic acid salt).

NMR (CDCl$_3$) 2.00 (m) 2HNH—CH$_2$—CH$_2$—CH$_2$—NH—; 3.45 (m) 4H—NH—CH$_2$—CH$_2$—CH$_2$—NH—; 10.0 (bs) —NH—CH$_2$—CH$_2$—CH$_2$—NH; 2.10 (m) 2HCO—CH$_2$—CH$_2$—CH$_2$—O-Ph; 2.60 (bt) 2HCO—CH$_2$—CH$_2$—CH$_2$—O-Ph; 3.99 (bt) CO—CH$_2$—CH$_2$—CH$_2$—O-Ph; 4.39 (t) 1H Ph-CH$_2$—CH—; 3.28 (m) 2H Ph-CH$_2$—CH—; 6.72 7.15 AA'BB' —O-Ph; 7.40 (d) Hc (H in ortho position of the nitrogen); 7.51 (dd) 1H Hb (H in meta position of the nitrogen); 7.68 (d) (H in ortho position of the sulphur); 12.91 (s) CO$_2$H.

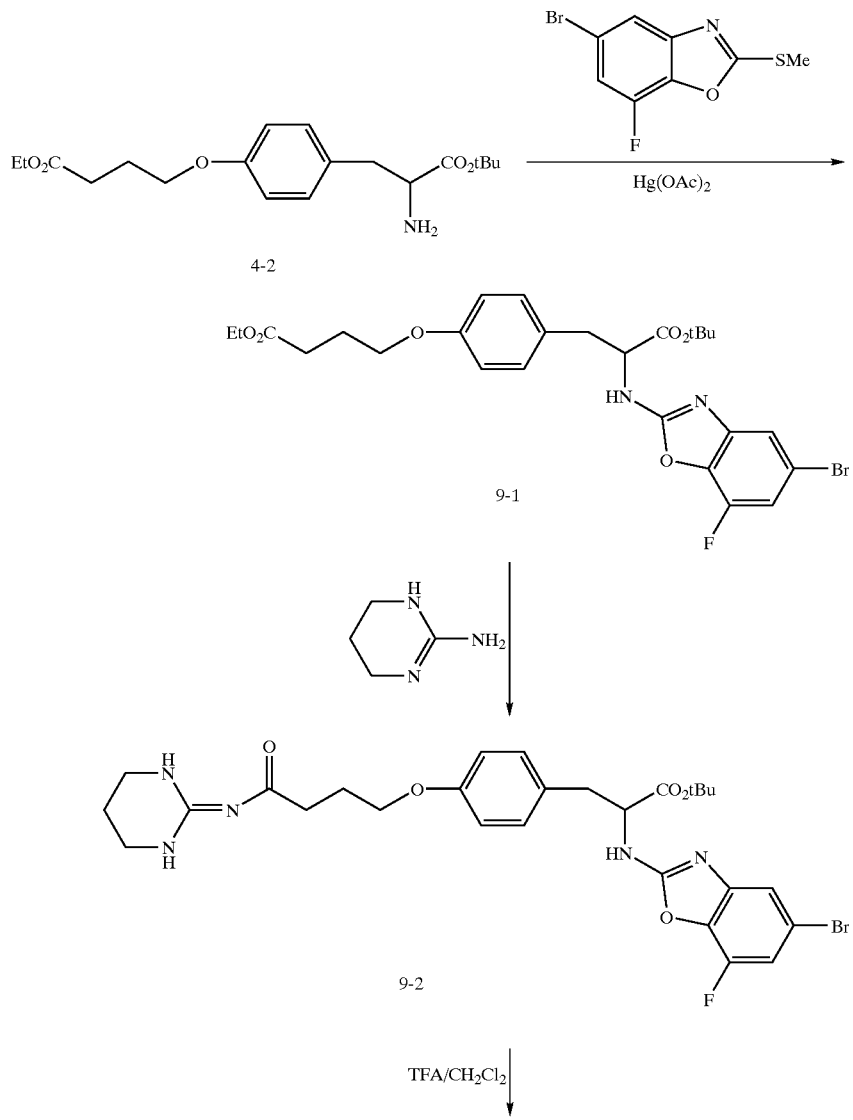

-continued

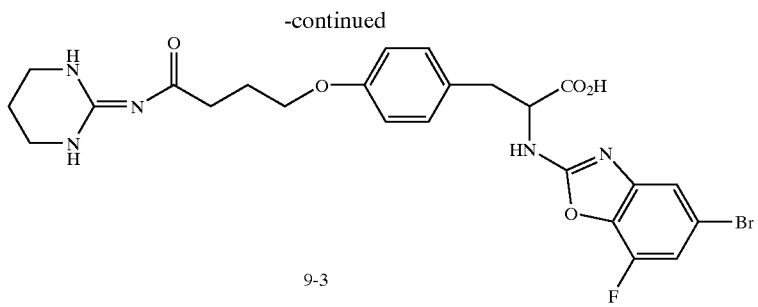

9-3

Example 9
N-[5-bromo-7-fluoro-2-benzoxazolyl)-O-[4-oxo-4-[(1,4,5,6-tetrahydro-2-pyrimidinyl)amino]butyl]-L-tyrosine
Preparation of 5-bromo-7-fluoro-2-(methylthio)-benzoxazole (P1)

A solution of 8.55 g of sodium dithionite in 40 ml of water is added to 2 g of 4-bromo-2-fluoro-6-nitro-phenol in 100 ml of ethanol, and the reaction medium is heated under reflux for 1 hour 30 minutes. After cooling down, the solution is filtered, evaporation is carried out until a dry extract is obtained which is taken up in ethyl acetate and washed, then the organic phase is dried. The residue (2-amino-4-bromo-6-fluoro-phenol) is re-evaporated under reduced pressure with 80 ml of methanol, 12.5 ml of water, 1.86 g of potassium ethyl xanthogenate and the reaction medium is heated under reflux for 4 hours (5-bromo-7-fluoro-2(3H)-benzoxazolethione is obtained). The reaction medium is left to cool down, 1.05 ml of methyl iodide is added, agitation is carried out overnight at ambient temperature followed by evaporating to dryness under reduced pressure. The residue is taken up in dichloromethane followed by washing, drying, filtering and concentrating the organic phase. The residue is then purified by chromatography, eluting with an AcOEt/Heptane mixture (20-80). 1.16 g of expected purified product is obtained.

(1,1-dimethyl ethyl) N-(5-bromo-7-fluoro-2-benzoxazolyl)-O-(4-ethoxy-4-oxo-butyl)-L-tyrosinate.(9-1)

The mixture constituted by aminoester 4-2 (865 mg; 2.46 mmoles), 5-bromo-7-fluoro-2-(methylthio)-benzoxazole (804 mg; 3.07 mmoles) and mercury diacetate (437 mg) is agitated for 3 hours, under nitrogen and at 100° C. After cooling down, the medium is chromatographed eluting with a $CH_2Cl_2$/ethyl acetate mixture 95/5, 564 mg of expected product is obtained, which is repurified by recrystallizing from isopropyl oxide. 528 mg of purified product is obtained.

NMR ($CDCl_3$) 1.22 (t); 1.40 (s); 2.05 (m); 2.45(m); 3.10 (m); 3.90 (m); 4.10 (q); 4.60 (m); 5.60 (d); 6.70–7.05 (AA'BB'); 7.00 (m); 7.20 (m).

(1,1-dimethyl ethyl) N-(5-bromo-7-fluoro-2-benzoxazolyl)-O-[4-oxo-4-[(1,4,5,6-tetrahydro-2-pyrimidinyl)amino]butyl]-L-tyrosinate (9-2)

Ester 9-1 (528 mg) is mixed with 2-amino-1,4,5,6-tetrahydropyrimidine (158+198+130 mg) in 10 ml of $CH_2Cl_2$ and agitation is carried out at ambient temperature for 16 hours. After evaporating under reduced pressure, the dry extract obtained is purified by chromatography eluting with a $CH_2Cl_2$/MeOH mixture 90/10. 260 mg of expected product 9-2 is obtained.

NMR ($CDCl_3$) 1.49 (s) 9HOC($CH_3$)$_3$; 1.99 (m) 2HNH—$CH_2$—C$\underline{H}_2$—$CH_2$—NH—; 3.44 (dd) 4H—NH—C$\underline{H}_2$—$CH_2$—$CH_2$—NH—; 2.12 (quint) 2HCO—$CH_2$—C$\underline{H}_2$—$CH_2$—O-Ph; 2.63 (t) 2HCO—C$\underline{H}_2$—$CH_2$—$CH_2$—O-Ph; 3.97 (t) CO—$CH_2$—$CH_2$—C$\underline{H}_2$—O-Ph; 4.68 (t) 1H Ph-$CH_2$—C$\underline{H}$—; 3.14 (dd)-3.24 (dd) 2H Ph-C$\underline{H}_2$—CH—; 6.79 7.06 AA'BB' —O-Ph; 6.99 (dd) J=1.5; 9.5 Hz 1H Hb (H in ortho position of the nitrogen); 7.28 (bd) J=1.5 Hz 1H Ha (H in para position of the nitrogen).

N-(5-bromo-7-fluoro-2-benzoxazolyl)-O-[4-oxo-4-[(1,4,5,6-tetrahydro-2-pyrimidinyl)amino]butyl]-L-tyrosine (9-3)

3.5 ml of trifluoroacetic acid is added to 260 mg of ester 9-2 in 5 ml of dichloromethane, agitation is carried out for 3 hours at ambient temperature then 10 ml of toluene is added. Evaporation is then carried out under reduced pressure and 236 mg of expected acid 9-3 is obtained.

IR ($CHCl_3$)
CO 1713 $cm^{-1}$; 1695 $cm^{-1}$
C=O C=N: 1666 $cm^{-1}$; 1649 $cm^{-1}$
Heterocycle+aromatic: 1612, 1595, 1586, 1558, 1513 $cm^{-1}$ NMR ($CDCl_3$) 1.99 (m) 2HNH—$CH_2$—C$\underline{H}_2$—$CH_2$—NH—; 2.06 (m) 2HCO—$CH_2$—C$\underline{H}_2$—$CH_2$—O-Ph; 2.62 (t) 2HCO—C$\underline{H}_2$—$CH_2$—O-Ph; 3.17 (dd)-3.28 (dd) 2H Ph-C$\underline{H}_2$—CH—; 3.44 (bs) 4H—NH—C$\underline{H}_2$—$CH_2$—C$\underline{H}_2$—NH—; 3.94 (t) CO—$CH_2$—$CH_2$—C$\underline{H}_2$—O-Ph; 4.77 (m) 1H Ph-$CH_2$—C$\underline{H}$—; 6.72 7.10 AA'BB' —O-Ph; 7.30 (m) Hb (H in ortho position of the nitrogen); 7.09 (m) (H in para position of the nitrogen); 9.87 (s) —N$\underline{H}$—$CH_2$—$CH_2$—$CH_2$—N$\underline{H}$; 12.66 (s) $CO_2H$.

MS 562+/[M+H]+

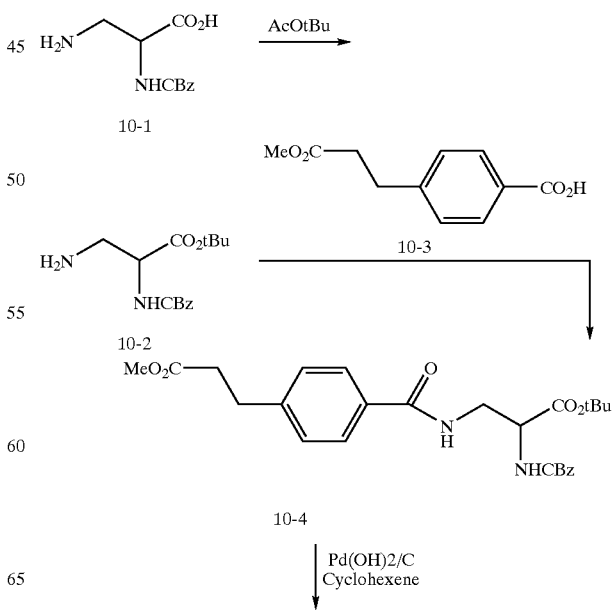

10-1

10-2

10-3

10-4

Pd(OH)2/C
Cyclohexene

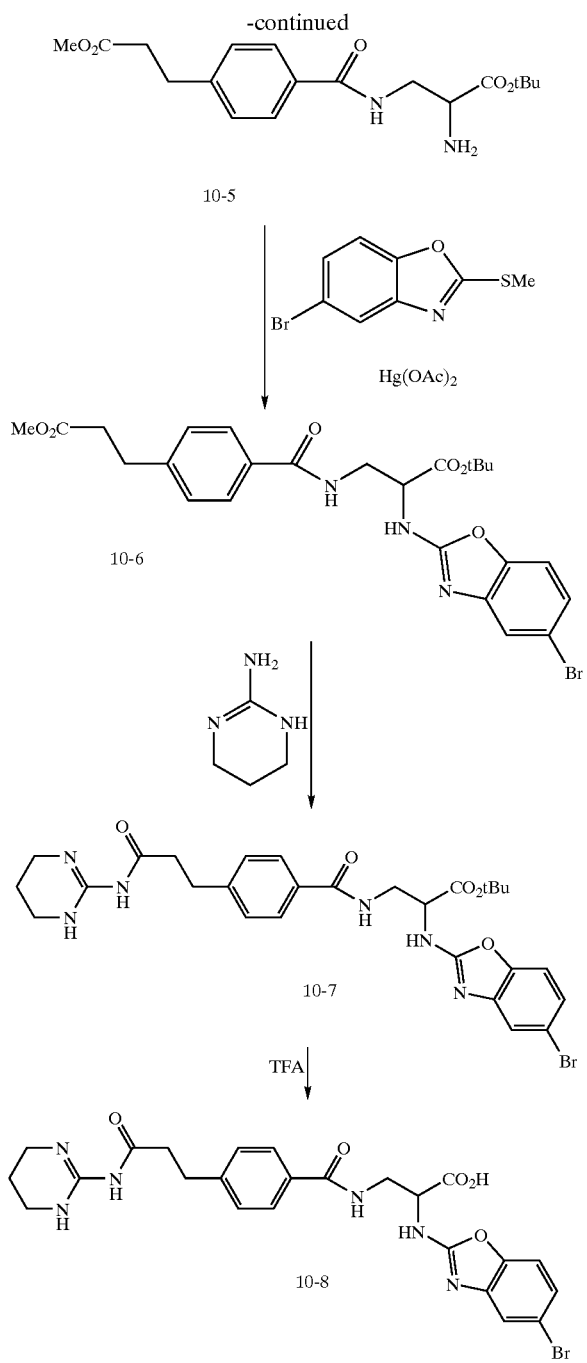

Example 10
N-(5-bromo-2-benzoxazolyl)-3-[[4-[3-oxo-3-[(1,4,5,6-tetrahydro-2-pyrimidinyl)amino]propyl]benzoyl]amino]-L-alanine (1,1-dimethyl ethyl) 3-amino-N-[(phenylmethoxy)carbonyl]-L-alaninate (10-2)

2.5 ml of concentrated $HClO_4$ is added without exceeding 5° C. to a suspension of 5 g of N-alpha-[(phenylmethoxy)carbonyl]-L-alpha,beta-diaminopropionic acid 10-1 (alternative nomenclature: (3-amino-N-[(phenylmethoxy)carbonyl]-L-alaninate) in 25 ml of tertbutyl acetate cooled down to 0° C., the temperature of the reaction medium is allowed to rise to 20° C. and agitation is carried out for 4 days at 20° C. The reaction medium is poured into a sodium bicarbonate/ice solution (300 ml/200 ml), followed by extracting with ethyl acetate, filtering, decanting, drying the organic phase, evaporating under reduced pressure until a dry extract is obtained corresponding to the expected product (3.2 g) which is used as it is in the following reaction.

(1,1-dimethyl ethyl) N-[phenylmethoxy)carbonyl]-3-[[4-(3-methoxy-3-oxo-propyl)benzoyl]amino]-L-alaninate (10-4)

566 mg of the acid ester 10-3 (methyl 4-carboxybenzenepropanoate) and 0.8 g of the aminoester 10-2 are mixed together, acetonitrile (30 ml) then EDCI (0.6 g) are added at 20° C. and the solution is agitated for 2 hours at 20° C. Dilution is then carried out with ethyl acetate followed by washing, drying the organic phase and evaporating under reduced pressure in order to obtain, after chromatography eluting with a $CH_2Cl_2$/AcOEt mixture 80/20, 1.30 g of expected product.

(1,1-dimethyl ethyl) 3-[[4-(3-methoxy-3-oxo-propyl)benzoyl]amino]-L-alaninate (10-5)

128 mg of $Pd(OH)_2$ on carbon is added to a solution of 10-4 (1.28 g, 2.64 mmol) in 35 ml of THF and 10 ml of cyclohexene, and the reaction medium is heated under reflux for 45 minutes. The temperature is brought down to approximately 20° C. followed by filtering, rinsing with ethyl acetate and evaporating under reduced pressure until a dry extract is obtained (724 mg) corresponding to the expected deprotected product.

(1,1-dimethyl ethyl) N-(5-bromo-2-benzoxazolyl)-3-[[4-(3-methoxy-3-oxo-propyl)benzoyl]amino]-L-alaninate (10-6)

A mixture constituted by 890 mg of 10-5, 620 mg of 5-bromo-2-methylthiobenzoxazole (prepared according to P1 but starting from 4-bromo-2-nitrophenol) and 350 mg of $Hg(OAc)_2$ is heated for 2 hours at 75° C. then for 2 hours at 95° C. The cooled down medium is chromatographed eluting with a $CH_2Cl_2$/AcOEt mixture 82/18. 159 mg of expected product is obtained.

Rf=0.28 ($CH_2Cl_2$/AcOEt 80/20)
IR ($CHCl_3$)
NH: 3387, 3242 $cm^{-1}$
C=O 1733 $cm^{-1}$
C=O, C=N: 1663, 1643 $cm^{-1}$
Aromatic+amide II: 1614, 1573, 1526, 1498 $cm^{-1}$ (1,1-dimethyl ethyl) N-(5-bromo-2-benzoxazolyl)-3-[[4-[3-oxo-3-[(1,4,5,6-tetrahydro-2-pyrimidinyl)amino]propyl]benzoyl]amino]-L-alaninate (10-7)

1,4,5,6-tetrahydro-2-pyrimidinamine (94 mg) is added to the ester 10-6 (140 mg) in 3 ml of THF, and agitation is carried out at ambient temperature for 4 hours. After evaporating under reduced pressure, the dry extract obtained is purified by chromatography eluting with a $CH_2Cl_2$/AcOEt 80/20 then $CH_2Cl_2$/MeOH 85/15 mixture. 71 mg of expected product 10-7 is obtained.

NMR ($CDCl_3$) 1.47 (s) 1.48 (s) 9HOC($CH_3$)$_3$; 1.92 (m) 2HNH—$CH_2$—C$\underline{H}_2$—$CH_2$—NH—; 3.35 (m) 4H—NH—C$\underline{H}_2$—$CH_2$—C$\underline{H}_2$—NH—; 2.65 (t) 2H CO—C$\underline{H}_2$—$CH_2$-Ph; 2.49 (t) 2HCO—$CH_2$—C$\underline{H}_2$-Ph; 3.97 (m) 2HNH—C$\underline{H}_2$—CH; 4.66 (dd) 4.89 (m) 1HNH—$CH_2$—C$\underline{H}$; 7.37 (bt) 1H N$\underline{H}$—$CH_2$—CH; 7.11 (d) 1H (H in ortho position of the oxygen); 7.17 (dd) 1H (H in meta position of the oxygen); 7.23 7.62 AA'BB' 7.26 7.71 AA'BB' -Ph-; 7.45 (d) 7.48 (d) 1H ((H in ortho position of the nitrogen).

N-(5-bromo-2-benzoxazolyl)-3-[[4-[3-oxo-3-[(1,4,5,6-tetrahydro-2-pyrimidinyl)amino]propyl]benzoyl]amino]-L-alanine (10-8)

Hydrolysis of the ester is carried out as in the previous examples, but starting from 56 mg of 10-7 and 2.5 ml of TFA in 2.5 ml of dichloromethane. 60 mg of 10-8 is obtained (in the form of the trifluoroacetic acid salt).

NMR (CDCl$_3$) 1.97 (m) 2H NH—CH$_2$—CH$_2$—CH$_2$—NH—; 2.77 (t) 2H CO—CH$_2$—CH$_2$-Ph; 2.93 (t) 2H CO—CH$_2$—CH$_2$-Ph; 3.42 (m) 4H—NH—CH$_2$—CH$_2$—CH$_2$—NH—; 4.05 (m) 2H NH—CH$_2$—CH; 4.72 (m) 4.90 (m) 1H NH—CH$_2$—CH; 7.22 (d) 1H (H in ortho position of the oxygen); 7.31 (dd) 1H (H in meta position of the oxygen); 7.17 7.69 AA'BB' -Ph-; 7.51 (bs) 10.03 and 10.55 mobile H's.
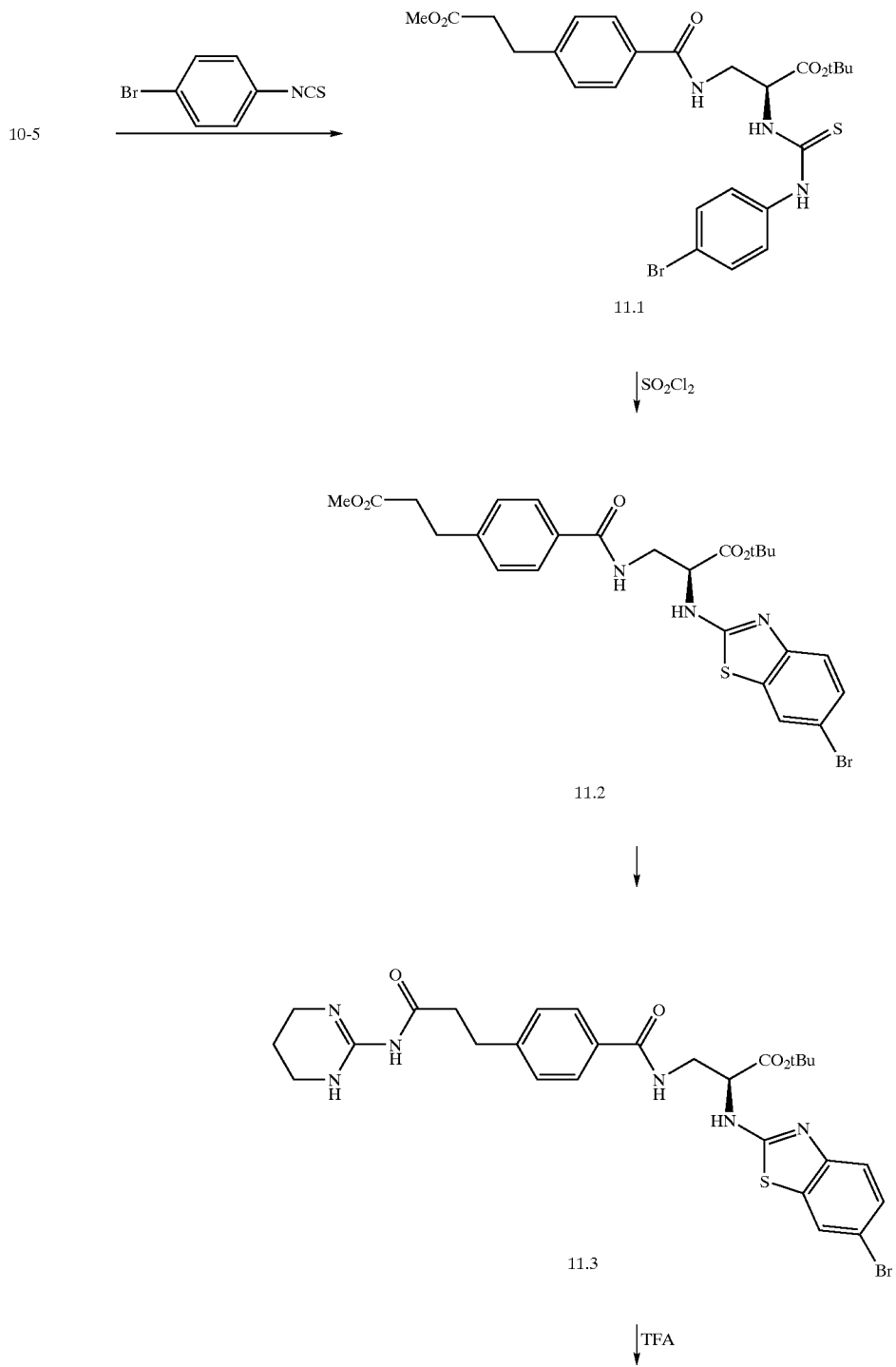

-continued

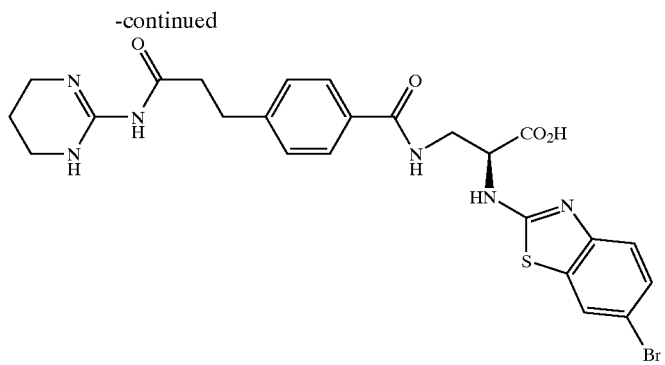

11.4

Example 11
N-(6-bromo-2-benzothiazolyl)-3-[[4-[3-oxo-3-[(1,4,5,6-tetrahydro-2-pyrimidinyl)amino]propyl]benzoyl]amino]-L-alanine (1,1-dimethyl ethyl) N-[[(4-bromophenyl)amino]thioxomethyl]-3-[[4-(3-methoxy-3-oxo-propyl)benzoyl]amino]-L-alaninate (11-1)

335 mg of (4-bromo-phenyl)isothiocyanate is added under nitrogen and at 0° C. to a solution of 500 mg of 10-5 (1,1-dimethyl ethyl) 3-[[4-(3-methoxy-3-oxo-propyl)benzoyl]amino]-L-alaninate in 12 ml of ethyl ether, and agitation is carried out for 1 hour while allowing the temperature to rise to 20° C. Evaporation is then carried out under reduced pressure until 500 mg of the expected crystallized product is obtained.

IR (CHCl$_3$)
NH: 3439 cm$^{-1}$, 3407 cm$^{-1}$+associated,
C=O: 1732 cm$^{-1}$; 1653 cm$^{-1}$
Conjugated system+aromatic+amide II: 1613, 1570, 1528, 1495 cm$^{-1}$ (1,1-dimethyl ethyl) N-(6-bromo-2-benzothiazolyl)-3-[[4-(3-methoxy-3-oxo-propyl)benzoyl]amino]-L-alaninate (11-2)

0.05 ml of SO$_2$Cl$_2$ is added to a solution of 250 mg of 11-1 in 5 ml of chlorobenzene cooled down to approximately 4° C., the temperature is allowed to rise to 20° C. and a further 0.05 ml of SO$_2$Cl$_2$ is added. The reaction medium is then diluted in dichloromethane and washed, the organic phase is dried, and evaporation is carried out under reduced pressure until a dry extract is obtained which is purified by chromatography, eluting with a CH$_2$Cl$_2$/AcOEt mixture 85/15. 70 mg of expected product is obtained.

IR (CHCl$_3$)
NH: 3388 cm$^{-1}$,
C=O: 1731 cm$^{-1}$; 1654 cm$^{-1}$
Conjugated system+aromatic+amide II: 1614, 1594, 1571, 1537, 1500 cm$^{-1}$ (1,1-dimethyl ethyl) N-(6-bromo-2-benzothiazolyl)-3-[[4-[3-oxo-3-[(1,4,5,6-tetrahydro-2-pyrimidinyl)amino]propyl]benzoyl]amino]-L-alaninate (11-3)

66 mg of 2-amino-1,4,5,6-tetrahydropyrimidine is added to a solution of 70 mg of 11-2 in 2 ml of THF, and agitation is carried out at ambient temperature for 3 hours. The reaction medium is then chromatographed eluting with a CH$_2$Cl$_2$/AcOEt mixture 80/20 then with MeOH/CH$_2$Cl$_2$ 10/90. 27 mg of expected product 11-3 is obtained.

MS
629$^+$/...=MH$^+$
573$^+$/...=MH$^+$-tBu/..

N-(6-bromo-2-benzothiazolyl)-3-[[4-[3-oxo-3-[(1,4,5,6-tetrahydro-2-pyimidinyl)amino]propyl]benzoyl]amino]-L-alanine (11-4)

Hydrolysis of the ester is carried out as in the previous examples, but starting from 27 mg of 11-3 and 1.3 ml of TFA in dichloromethane. 33 mg of 11-4 is obtained (in the form of the trifluoroacetic acid salt).

NMR (CDCl$_3$) 1.98 (m) 2HNH—CH$_2$—CH$_2$—CH$_2$—NH—; 2.78 (bt) 2H CO—CH$_2$—CH$_2$-Ph; 2.94 (bt) 2HCO—CH$_2$—CH$_2$-Ph; 3.42 (m) 4H—NH—CH$_2$—CH$_2$—CH$_2$—NH—; 4.01 (bs) 4.12 (bs) 2HNH—CH$_2$—CH; 4.45 (bs) 1HNH—CH$_2$—CH; 7.38 (d) 1H (H in ortho position of the nitrogen); 7.51 (bd) 1H (H in meta position of the nitrogen); 7.70 (bs) 1H (H in ortho position of the sulphur); 7.19 7.74 AA'BB' -Ph-; 7.96 (bs) 1H mobile H; 10.10 (bs) 2H (NH); 13.15 (s) 1HCO$_2$H.

The following examples are also prepared according to the operating methods indicated above.

Example 12
N-(7-fluoro-2-benzoxazolyl)-O-[4-oxo-4-[(1,4,5,6-tetrahydro-2-pyrimidinyl)amino]butyl]-L-tyrosine NMR (DMSO) 1.85 (m) 2HNH—CH$_2$—CH$_2$—CH$_2$—NH—; 1.97 (quint) 2HCO—CH$_2$—CH$_2$—CH$_2$—O-Ph; 2.91 (dd) 3.15 (dd) 2H Ph-CH$_2$—CH—NH; 2.55 (bt) 2HCO—CH$_2$—CH$_2$—CH$_2$—O-Ph; 3.35 (m) 4H—NH—CH$_2$—CH$_2$—CH$_2$—NH—; 3.95 (t) 2H CO—CH$_2$—CH$_2$—CH$_2$—O-Ph; 4.39 (t) 1H Ph-CH$_2$—CH—; 6.82 7.23 AA'BB'—O-Ph; 6.90 (ddd) (H in para position of the nitrogen); 7.07 (m) 2H b (H in ortho and meta positions of the nitrogen); 8.64 (bd) 1HNH; 8.94 (bs) —NH—CH$_2$—CH$_2$—CH$_2$—NH; 11.50 (s) 12.93 (s) mobile H's.

Example 13
N-(6-fluoro-2-benzoxazolyl)-O-[4-oxo-4-[(1,4,5,6-tetrahydro-2-pyrimidinyl)amino]butyl]-L-tyrosine

MS 484$^+$ [M+H]$^+$

NMR (DMSO) 1.84 (m) 2HNH—CH2—CH2—CH2-NH; 1.97 (quint) 2HCO—CH2—CH2—CH2-O; 2.53 (m) 2HCO—CH2; 2.90 and 3.14 (2dd) 2H Ph-CH2; 3.34 (bs) 4HNH—CH2-CH2-CH2-NH; 3.94 (t) 2HCH2-O; 4.34 (m) 1H Ph-CH2-CH—NH; 6.81 and 7.22 (AA'BB') 4H-Ph-; 6.95 (ddd) 1H (H in meta position of the nitrogen); 7:19 (dd) 1H (H ortho nitrogen); 7.35 (dd) 1H (H in ortho position of the oxygen); 8.43 (bd) 1H (NH—CH); 8.88 (bs) 2H (NH—CH2); 11.40(s) and 12.94 (bs) mobile H's

Example 14
N-(5-fluoro-2-benzoxazolyl)-O-[4-oxo-4-[(1,4,5,6-tetrahydro-2-pyrimidinyl)amino]butyl]-L-tyrosine trifluoroacetate NMR (CDCl$_3$) 2.01 (m) 2HNH—CH$_2$—CH$_2$—CH$_2$—NH—; 2.07 (m) 2HCO—CH$_2$—C H₂—CH₂—O-Ph; 3.16 (dd) 3.31 (dd) 2H Ph-CH₂—CH—NH; 2.60 (m) 2HCO—CH₂—CH₂—CH₂—O-Ph; 3.46 (m) 4H—NH-CH₂—CH₂—CH₂—NH—; 3.92 (m) 2HCO—CH₂—CH₂—CH₂—O-Ph; 4.75 (dd) 1H Ph-CH₂—CH—; 5.84 mobile 1H; 6.72 7.15 AA'BB' —O-Ph; 6.93 (td) (H in para position of the nitrogen); 7.15 (masked) (H in ortho position of the nitrogen); 7.26 (masked) (H in ortho position of the oxygen); 9.84 (bs) 2H NH—CH₂—CH₂—CH₂—NH; 12.63 (s) 1HCO₂H.

Example 15
N-(7-chloro-2-benzoxazolyl)-O-[4-oxo-4-[(1,4,5,6-tetrahydro-2-pyrimidinyl)amino]butyl]-L-tyrosine trifluoroacetate
NMR (CDCl₃) 1.89 (m) 2HNH—CH₂—CH₂—CH₂—NH—; 2.00 (quint) 2HCO—CH₂—CH₂—CH₂—O-Ph; 2.98 (dd) 3.18 (dd) 2H Ph-CH₂—CH—NH; 2.55 (t) 2HCO—CH₂—CH₂—CH₂—O-Ph; 3.37 (m) 4H—NH—CH₂—CH₂—CH₂—NH—; 3.98 (t) CO—CH₂—CH₂—CH₂—O-Ph; 4.43 (m) 1H Ph-CH₂—CH—; 6.81 7.22 AA'BB' —O-Ph; 7.03 (dd) 7.18 (dd) (H in ortho and para positions of the nitrogen); 7.11 (m) 1H b (H in meta position of the nitrogen); 8.64 (bd) 1HNH; 8.95 (bs) NH—CH₂—CH₂—CH₂—NH; 11.39 (bs) 1HCO₂H.

Example 16
N-(6-chloro-2-benzoxazolyl)-O-[4-oxo-4-[(1,4,5,6-tetrahydro-2-pyrimidinyl)amino]butyl]-L-tyrosine
MS 500⁺ MH⁺; 522⁺ MNa⁺
NMR (DMSO) 1.84 (m) 2HNH—CH2-CH2-CH2-NH; 1.96 (m) 2HCO—CH2-CH2-CH2-O; 2.52 (m) 2HCO—CH2; 2.90 and 3.14 (2dd) 2H Ph-CH2; 3.34 (m) 4HNH—CH+b 2-CH2-CH2-NH; 3.94 (t) 2HCH2-O; 4.35 (m) 1H Ph-CH2-CH—NH; 6.82 and 7.21 (AA'BB') 4H-Ph-; 7.15 (dd) 1H (H in meta position of the nitrogen); 7.21 (d) 1H (H in ortho position of the nitrogen); 7.52 (d) 1H (H in ortho position of the oxygen); 8.53 (bd) 1H (NH—CH); 8.84 (bs) mobile H's Example 17
N-(5-chloro-2-benzoxazolyl)-O-[4-oxo-4-[(1,4,5,6-tetrahydro-2-pyrimidinyl)amino]butyl]-L-tyrosine
MS 500⁺ [MH]⁺
NMR (CDCl3) 1.99 (m) 4HNH—CH2-CH2-CH2-NH and CO—CH2-CH2-CH2-O; 2.46 (m) 2HCO—CH2; 3.22 and 3.32 (2dd) 2H Ph-CH2; 3.41 (m) 4HNH—CH2-CH2-CH2-NH; 3.88 (bt) 2HCH2-O; 4.62 (bs) 1H Ph-CH2-CH—NH; 6.70 and 7.09 (AA'BB') 4H-Ph-; 6.97 (d) 1H (H in ortho position of the oxygen); 7.09 (m) 1H (H in meta position of the oxygen); 7.33 (bs) 1H (H in ortho position of the nitrogen); 10.44 (bs) and 10.64 (bs) and 14.00 (bs) mobile H's Example 18
N-(5-bromo-2-benzoxazolyl)-O-[4-oxo-4-[(1,4,5,6-tetrahydro-2-pyrimidinyl)amino]butyl]-L-tyrosine trifluoroacetate
NMR (CDCl₃) 2.01 (m) 2HNH—CH₂—CH₂—CH₂—NH—; 2.10 (m) 2HCO—CH₂—CH₂—O-Ph; 2.58 (m) 2HCO—CH₂—CH₂—CH₂—O-Ph; 3.21 (dd) 3.29 (dd) 2H Ph-CH₂—CH—NH; 3.47 (bs) 4H—NH—CH₂—CH₂—CH₂—NH—; 3.97 (m) 2HCO—CH₂—CH₂—CH₂—O-Ph; 4.79 (dd) 1H Ph-CH₂—CH—; 4.95 (bs) mobile H's; 6.72 7.15 AA'BB' —O-Ph; 7.22 (d) (H in ortho position of the oxygen); 7.36 (dd) (H in para position of the nitrogen); 7.58 (d) (H in ortho position of the nitrogen); 9.72 (bs) 2H NH—CH₂—CH₂—CH₂—NH; 12.45 (bs) 1HCO₂H.

Example 19
N-(naphth[2,3-d]oxazol-2-yl)-O-[4-oxo-4-[(1,4,5,6-tetrahydro-2-pyrimidinyl)amino]butyl]-L-tyrosine
MS 516⁺ MH⁺
NMR (DMSO) 1.78 (m) 2HNH—CH2-CH2-CH2-NH; 1.91 (m) 2HCO—CH2-CH2-CH2-O; 2.35 (m) 2HCO—CH2; 2.94 and 3.24 (2dd) 2H Ph-CH2; 3.24 (m) 4HNH—CH2-CH2-CH2-NH; 3.89 (t) 2HCH2-O; 4.23 (m) 1H Ph-CH2-CH—NH; 6.78 and 7.12 (AA'BB') 4H-Ph-; 7.34 (m) 2H (aromatic H's); 7.56 (s) 1H (aromatic H); 7.72 (s) 1H (aromatic H); 7.84 (m) 2H (aromatic H's); 8.03 (bd) 1H (NH—CH)

Example 20
N-(naphth[1,2-d]oxazol-2-yl)-O-[4-oxo-4-[(1,4,5,6-tetrahydro-2-pyrimidinyl)amino]butyl]-L-tyrosine
MS 516⁺ MH⁺
NMR (DMSO) 1.82 (m) 2HNH—CH2-CH2-CH2-NH; 1.94 (m) 2HCO—CH2-CH2-CH2-O; 2.49 (m) 2HCO—CH2; 2.96 and 3.18 (2dd) 2H Ph-CH2; 3.33 (m) 4HNH—CH2-CH2-CH2-NH; 3.93 (t) 2HCH2-O; 4.46 (m) 1H Ph-CH2-CH—NH; 6.82 and 7.26 (AA'BB') 4H-Ph-; 7.43 (m) 1H (aromatic H); 7.52 (m) 1H (aromatic H); 7.56 (m) 1H (H in meta position of the oxygen); 7.63 (m) 1H (H in ortho position of the oxygen); 7.95 (d) 1H (aromatic H); 8.10 (d) 1H (aromatic H); 8.39 (bd) 1H (NH—CH); 8.96 (bs) mobile H's Example 21
O-[4-oxo-4-[(1,4,5,6-tetrahydro-2-pyrimidinyl)amino]butyl]-N-(5-phenyl-2-benzoxazolyl)-L-tyrosine
MS 542⁺ MH⁺
NMR (DMSO) 1.83 (m) 2HNH—CH2-CH2-CH2-NH; 1.97 (m) 2HCO—CH2-CH2-CH2-O; 2.54 (m) 2HCO—CH2; 2.93 and 3.16 (2dd) 2H Ph-CH2; 3.34 (m) 4HNH—CH2-CH2-CH2-NH; 3.95 (t) 2HCH2-O; 4.40 (m) 1H Ph-CH2-CH—NH; 6.83 and 7.24 (AA'BB')-Ph-; 7.27 (dd) 1H (H in meta position of the nitrogen); 7.33 (bt) 1H (aromatic H); 7.41 (d) 1H (H ortho oxygen); 7.43 (m) 2H (aromatic H's); 7.48 (d) 1H (H in ortho position of the nitrogen); 7.62 (bd) 2H (aromatic H's); 8.45 (bd) 1H (NH—CH); 8.75 (bs) and 11.26 (bs) and 12.97 (bs) mobile H's Example 22
N-(6-nitro-2-benzoxazolyl)-O-[4-oxo-4-[(1,4,5,6-tetrahydro-2-pyrimidinyl)amino]butyl]-L-tyrosine
MS 511⁺ MH⁺
NMR (CDCl3) 2.00 (m) 2HNH—CH2-CH2-CH2-NH; 2.05 (m) 2HCO—CH2-CH2-CH2-O; 2.48 (m) 2HCO—CH2; 3.30 (m) 2H Ph-CH2; 3.44 (m) 4HNH—CH2-CH2-CH2-NH; 3.91 (t) 2HCH2-O; 4.69 (bs) 1H Ph-CH2-CH—NH; 6.71 and 7.08 (AA'BB') 4H-Ph-; 7.35 (d) 1H (H in ortho position of the nitrogen); 8.02 (bs) 1H (H in ortho position of the oxygen); 8.16 (dd) 1H (H in meta position of the nitrogen); 10.56 (bs) and 13.91 (bs) mobile H's Example 23
O-[4-oxo-4-[(1,4,5,6-tetrahydro-2-pyrimidinyl)amino]butyl]-N-[5-(trifluoromethyl)-2-benzoxazolyl]-L-tyrosine
MS 534⁺ MH⁺
NMR (CDCl3) 1.99 (m) 2HNH—CH2-CH2-CH2-NH; 2.04 (m) 2HCO—CH2-CH2-CH2-O; 2.53 (m) 2HCO—CH2; 3.22 and 3.33 (2dd) 2H Ph-CH2; 3.43 (m) 4HNH—CH2-CH2-CH2-NH; 3.90 (bt) 2HCH2-O; 4.70 (bt) 1H Ph-CH2-CH—NH; 6.71 and 7.09 (AA'BB') 4H-Ph-; 7.30 (m) 2H (H on the oxygen side); 7.59 (bs) 1H (H in ortho position of the nitrogen); 10.37 (bs) and 13.61 (bs) mobile H's

Example 24
N-(oxazolo[5,4-b]pyridin-2-yl)-O-[4-oxo-4-[(1,4,5,6-tetrahydro-2-pyrimidinyl)amino]butyl]-L-tyrosine

Example 25
N-(oxazolo[4,5-b]pyridin-2-yl)-O-[4-oxo-4-[(1,4,5,6-tetrahydro-2-pyrimidinyl)amino]butyl]-L-tyrosine NMR (CDCl3) 2.01 (m) 2HNH—CH2-CH2-CH2-NH; 2.05 (m) 2HCO—CH2-CH2-CH2-O; 2.51 (bt) 2HCO—CH2; 3.25 and 3.37 (2m) 2H Ph-CH2; 3.44 (m) 4HNH—CH2-CH2-CH2-NH; 3.92 (bt) 2HCH2-O; 4.83 (bs) 1H Ph-CH2-CH—NH; 6.72 and 7.09 (AA'BB') 4H-Ph-; 6.95 (dd) 1H (aromatic H); 7.26 (m) 1H (aromatic H); 7.46 (m) 1H (aromatic H); 10.37 (bs) and 13.40 (bs) mobile H's

Example 26
O-[4-oxo-4-[(1,4,5,6-tetrahydro-2-pyrimidinyl)amino]butyl]-N-[5-(trifluoromethyl)-oxazolo[4,5-b]pyridin-2-yl]-L-tyrosine

Example 27
N-(6,7-difluoro-2-benzoxazolyl)-O-[4-oxo-4-[(1,4,5,6-tetrahydro-2-pyrimidinyl)amino]butyl]-L-tyrosine

MS 502$^+$ MH$^+$

NMR (DMSO) 1.89 (q) 2HNH—CH2-CH2-CH2-NH; 2.02 (m) 2HCO—CH2-CH2-CH2-O; 2.57 (bt) 2HCO—CH2; 2.84 and 3.04 (2dd) 2H Ph-CH2; 3.39 (m) 4H NH—CH2-CH2-CH2-NH; 4.00 (bt) 2HCH2-O; 4.42 (m) 1H Ph-CH2-CH—NH; 6.70 (ddd) 1H (H in meta position of the nitrogen); 6.84 and 7.19 (AA'BB') 4H-Ph-; 7.03 (bd) 1H (NH—CH); 7.48 (ddd) 1H (H ortho nitrogen); 8.75 (bs) and 10.31 (bs) mobile H's

Example 28
N-(5,7-dichloro-2-benzoxazolyl)-O-[4-oxo-4-[(1,4,5,6-tetrahydro-2-pyrimidinyl)amino]butyl]-L-tyrosine

MS 534$^+$ MH$^+$

NMR (DMSO) 1.94 (m) 2HNH—CH2-CH2-CH2-NH; 1.96 (m) 2HCO—CH2-CH2-CH2-O; 2.51 (m) 2HCO—CH2; 2.90 and 3.16 (2dd) 2H Ph-CH2; 3.35 (m) 4HNH—CH2-CH2-CH2-NH; 3.94 (bt) 2HCH2-O; 4.34 (m) 1H Ph-CH2-CH—NH; 6.82 and 7.21 (AA'BB') 4H-Ph-; 7.20 (d) and 7.29 (d) 2H (aromatic H's); 8.91 (m) (NH—CH); 9.00 (bs) mobile H

Example 29
N-(5,7-dichloro-6-methyl-2-benzoxazolyl)-O-[4-oxo-4-[(1,4,5,6-tetrahydro-2-pyrimidinyl)amino]butyl]-L-tyrosine

MS 548$^+$ MH$^+$

NMR (DMSO) 1.81 (m) and 1.88 (m) 2HNH—CH2-CH2-CH2-NH; 1.99 (m) 2HCO—CH2-CH2-CH2-O; 2.32 (s) 3H CH3; 2.54 (m) 2HCO—CH2; 2.83 and 3.02 (m) 2H Ph-CH2; 3.23 and 3.38 (2m) 4HNH—CH2-CH2-CH2-NH; 3.97 (m) 2HCH2-O; 4.16 and 4.40 (2m) 1H Ph-CH2-CH—NH; 6.75 and 7.15 (AA'BB') 4H-Ph-; 7.90 (s) 1H (aromatic H); 8.82 (m) (NH—CH)

Example 30
N-[5-[(phenylamino)sulphonyl]-2-benzoxazolyl]-O-[4-oxo-4-[(1,4,5,6-tetrahydro-2-pyrimidinyl)amino]butyl]-L-tyrosine

MS 621$^+$ MH$^+$

NMR (DMSO) 1.84 (m) 2HNH—CH2-CH2-CH2-NH; 1.96 (m) 2HCO—CH2-CH2-CH2-O; 2.51 (m) 2HCO—CH2; 2.90 and 3.14 (2dd) 2H Ph-CH2; 3.34 (m) 4HNH—CH2-CH2-CH2-NH; 3.93 (bt) 2HCH2-O; 4.36 (m) 1H Ph-CH2-CH—NH; 6.80 and 7.20 (AA'BB') 4H-Ph-; 6.98 (bt) 1H (aromatic H); 7.07 (bd) 2H (aromatic H's); 7.20 (m) 2H (aromatic H's); 7.40 (dd) 1H (H in meta position of the oxygen); 7.49 (d) 1H (H in ortho position of the oxygen); 7.51 (bs) 1H (H in ortho position of the nitrogen); 8.75 (bd) 1H (NH—CH); 8.86 (bs) and 10.20 (bs) mobile H's

Example 31
N-[5-[(N-methylphenylamino)sulphonyl]-2-benzoxazolyl]-O-[4-oxo-4-[(1,4,5,6-tetrahydro-2-pyrimidinyl)amino]butyl]-L-tyrosine

MS 635$^+$ MH$^+$

NMR (DMSO) 1.84 (m) 2HNH—CH2-CH2-CH2-NH; 1.96 (m) 2HCO—CH2-CH2-CH2-O; 2.53 (m) 2HCO—CH2; 2.91 and 3.15 (2dd) 2H Ph-CH2; 3.11 (s) 3H CH3; 3.35 (m) 4HNH—CH2-CH2-CH2-NH; 3.94 (t) 2H CH2-O; 4.38 (m) 1H Ph-CH2-CH—NH; 6.82 and 7.23 (AA'BB') 4H-Ph-; 7.08 (bd) 3H (aromatic H's+H in meta position of the oxygen); 7.27 (m) 1H (H in ortho position of the nitrogen); 7.51 (d) 1H (H in ortho position of the oxygen); 7.20 to 7.35 (m) 3H (aromatic H's); 8.80 (bs) 1H (NH—CH); 8.85 (bs) and 11.37 (bs) and 13.04 (bs) mobile H's

Example 32
N-(6-chloro-2-benzothiazolyl)-O-[4-oxo-4-[(1,4,5,6-tetrahydro-2-pyrimidinyl)amino]butyl]-L-tyrosine MS 516$^+$ MH$^+$; 538$^+$ MNa$^+$ NMR (DMSO) 1.84 (m) 2HNH—CH2-CH2-CH2-NH; 1.97 (m) 2HCO—CH2-CH2-CH2-O; 2.52 (m) 2HCO—CH2; 2.90 and 3.10 (2dd) 2H Ph-CH2; 3.34 (m) 4H NH—CH2-CH2-CH2-NH; 3.95 (t) 2HCH2-O; 4.56 (m) 1H Ph-CH2-CH—NH; 6.82 and 7.19 (AA'BB') 4H-Ph-; 7.22 (dd) 1H (H in meta position of the nitrogen); 7.33 (d) 1H (H in ortho position of the nitrogen); 7.79 (d) 1H (H in ortho position of the sulphur); 8.52 (bd) 1H (NH—CH); 8.85 (bs) and 11.39 (bs) mobile H's

Example 33
N-(7-bromo-2-benzothiazolyl)-O-[4-oxo-4-[(1,4,5,6-tetrahydro-2-pyrimidinyl)amino]butyl]-L-tyrosine

MS 560$^+$ MH$^+$

NMR (CDCl3) 2.00 (m) 2HNH—CH2-CH2-CH2-NH; 2.11 (m) 2HCO—CH2-CH2-CH2-O; 2.61 (m) 2HCO—CH2; 3.30 (m) 2H Ph-CH2; 3.45 (m) 4HNH—CH2-CH2-CH2-NH; 4.00 (bt) 2HCH2-O; 4.36 (bt) 1H Ph-CH2-CH—NH; 6.74 and 7.17 (AA'BB') 4H-Ph-; 7.31 (m) 1H (H in meta position of the nitrogen); 7.38 (bd) 1H (aromatic H); 7.49 (bd) 1H (aromatic H); 9.94 (bs) and 12.82 (bs) mobile H's

Example 34
N-(5-bromo-2-benzothiazolyl)-O-[4-oxo-4-[(1,4,5,6-tetrahydro-2-pyrimidinyl)amino]butyl]-L-tyrosine

MS 560$^+$ MH$^+$

NMR (CDCl3) 2.01 (m) 2HNH—CH2-CH2-CH2-NH; 2.10 (quint b) 2HCO—CH2-CH2-CH2-O; 2.59 (m) 2HCO—CH2; 3.29 (m) 2H Ph-CH2; 3.46 (bs) 4H NH—CH2-CH2-CH2-NH; 4.00 (bt) 2HCH2-O; 4.30 (m) 1H Ph-CH2-CH—NH; 6.74 and 7.17 (AA'BB') 4H-Ph-; 7.26 (m) 1H (H in meta position of the sulphur); 7.40 (m) 1H (H in ortho position of the sulphur); 7.69 (d) 1H (H in ortho position of the nitrogen); 9.83 (bs) and 12.62 (bs) mobile H's

Example 35
N-(1H-benzimidazol-2-yl)-O-[4-oxo-4-[(1,4,5,6-tetrahydro-2-pyrimidinyl)amino]butyl]-L-tyrosine

MS 465$^+$ MH$^+$

NMR (DMSO) 1.89 (m) 2HNH—CH2-CH2-CH2-NH; 1.96 (m) 2HCO—CH2-CH2-CH2-O; 2.54 (m) 2HCO—

CH2; 3.03 and 3.22 (2dd) 2H Ph-CH2; 3.36 (m) 4HNH—CH2-CH2-CH2-NH; 3.92 (m) 2HCH2-O; 4.64 (m) 1H Ph-CH2-CH—NH; 6.83 and 7.19 (AA'BB') 4H-Ph-; 7.24 (m) 2H (aromatic H's); 7.38 (m) 2H (aromatic H's)

Example 36
N-(5-nitro-2-benzoxazolyl)-O-[4-oxo-4-[(1,4,5,6-tetrahydro-2-pyrimidinyl)amino]butyl]-L-tyrosine NMR (CDCl3) 2.05 (bs) 2HNH—CH2-CH2-CH2-NH; 2.09 (m) 2HCO—CH2-CH2-CH2-O; 2.64 (bs) 2HCO—CH2; 3.23 and 3.39 (2bd) 2H Ph-CH2; 3.50 (bs) 4HNH—CH2-CH2-CH2-NH; 3.92 (bs) 2HCH2-O; 4.79 (bs) 1H Ph-CH2-CH—NH; 6.75 and 7.16 (AA'BB') 4H-Ph-; 7.29 (m) 1H (H in ortho position of the oxygen); 8.05 (bd) 1H (H in meta position of the oxygen); 8.18 (bs) 1H (H in ortho position of the nitrogen); 9.71 (bs) and 12.86 (bs) mobile H's.

Example 37
N-(4-nitro-2-benzoxazolyl)-O-[4-oxo-4-[(1,4,5,6-tetrahydro-2-pyrimidinyl)amino]butyl]-L-tyrosine NMR (DMSO) 1.81 (bs) 2HNH—CH2-CH2-CH2-NH; 1.90 (bs) 2HCO—CH2-CH2-CH2-O; 2.50 (m) 2HCO—CH2; 2.90 and 3.18 (2dd) 2H Ph-CH2; 3.31 (bs) 4H NH—CH2-CH2-CH2-NH; 3.91 (bs) 2HCH2-O; 4.32 (bs) 1H Ph-CH2-CH—NH; 6.80 and 7.12 (AA'BB') 4H-Ph-; 7.07 (bt) 1H (H in meta position of the oxygen); 7.67 (bd) 1H (aromatic H); 7.87 (bd) 1H (aromatic H); 10.2 (bs) 10.8 (bs) mobile H's.

Example 38
N-(6-ethylsulphonyl-2-benzoxazolyl)-O-[4-oxo-4-[(1,4,5,6-tetrahydro-2-pyrimidinyl)amino]butyl]-L-tyrosine NMR (CDCl3) 1.27 (bt) 3H CH3; 2.01 (bs) 4HNH—CH2-CH2-CH2-NH and CO—CH2-CH2-CH2-O; 2.50 (bs) 2HCO—CH2; 3.18 (quint b) 2HCH2-SO2; 3.28 (bs) 2H Ph-CH2; 3.43 (bs) 4HNH—CH2-CH2-CH2-NH; 3.88 (bs) 2H CH2-O; 4.68 (bs) 1H Ph-CH2-CH—NH; 6.71 and 7.09 (AA'BB') 4H-Ph-; 7.31 (bs) 1H (H in ortho position of the oxygen); 7.61 (bd) 1H (H in meta position of the oxygen); 7.86 (bs) 1H (H in ortho position of the nitrogen); 10.57 (bs) and 13.88 (bs) mobile H's.

Example 39
N-(4,5,6,7-tetrafluoro-2-benzoxazolyl)-O-[4-oxo-4-[(1,4,5,6-tetrahydro-2-pyrimidinyl)amino]butyl]-L-tyrosine NMR (CDCl3) 2.00 (bs) 2HNH—CH2-CH2-CH2-NH; 2.07 (m) 2HCO—CH2-CH2-CH2-O; 2.51(m) 2HCO—CH2; 3.28 (m) 2H Ph-CH2; 3.44 (bs) 4HNH—CH2—CH2-CH2-NH; 3.95 (bt) 2HCH2-O; 4.70 (bs) 1H Ph-CH2-CH—NH; 6.59 (bs) 1H NH—CH—CH2; 6.72 and 7.07 (AA'BB') 4H-Ph-; 10.36 (bs) and 13.54 (bs) mobile H's.

Example 40
N-(4-methyl-2-benzoxazolyl)-O-[4-oxo-4-[(1,4,5,6-tetrahydro-2-pyrimidinyl)amino]butyl]-L-tyrosine NMR (CDCl3) 1.99 (m) 4HNH—CH2-CH2-CH2-NH and CO—CH2-CH2; 2.44 (m) 2HCO—CH2; 2.47 (s) 3H CH3; 3.22 and 3.33 (2dd) 2H Ph-CH2; 3.42 (m) 4HNH—CH2-CH2-CH2-NH; 3.87 (bt) 2HCH2-O; 4.69 (bt) 1H Ph-CH2-CH—NH; 6.71 and 7.11 (AA'BB') 4H-Ph-; 6.96 (m) 2H and 7.08 (m) 3H (aromatic H's); 10.68 (bs) and 13.97 (bs) mobile H's.

Example 41
N-(5-methoxy-2-benzoxazolyl)-O-[4-oxo-4-[1,4,5,6-tetrahydro-2-pyrimidinyl)amino]butyl]-L-tyrosine NMR (DMSO) 1.83 (m) 2HNH—CH2-CH2-CH2-NH; 1.96 (m) 2HCO—CH2-CH2-CH2-O; 2.50 (m) 2HCO—CH2; 2.90 and 3.13 (2dd) 2H Ph-CH2; 3.34 (m) 4HNH—CH2-CH2-CH2-NH; 3.71 (s) 3H CH3; 3.93 (bt) 2HCH2-O; 4.31 (ddd) 1H Ph-CH2-CH—NH; 6.51 (dd) 1H (H in meta position of the oxygen); 6.81 and 7.12 (AA'BB') 4H-Ph-; 6.81 (m) 1H (H in ortho position of the nitrogen); 7.19 (m) 1H (H in ortho position of the oxygen); 8.21 (bd) 1H (NH—CH); 9.15 (bs) and 12.45 (bs) mobile 3H's.

Example 42
N-(4-hydroxy-2-benzoxazolyl)-O-[4-oxo-4-[(1,4,5,6-tetrahydro-2-pyrimidinyl)amino]butyl]-L-tyrosine NMR (DMSO) 1.80 (m) 2H NH—CH2-CH2-CH2-NH; 1.92 (m) 2HCO—CH2-CH2-CH2-O; 2.40 (m) 2HCO—CH2; 2.90 and 3.16 (dd) 2H Ph-CH2; 3.28 (bs) 4H NH—CH2-CH2-CH2-NH; 3.91 (bt) 2HCH2-O; 4.20 (m) 1H Ph-CH2-CH—NH; 6.78 and 7.10 (AA'BB') 4H-Ph-; 6.54 (m) and 6.76 (m) 3H (aromatic H's); 7.50 (bd) 1H (NH—CH); 9.52 (bs) and 10.18 (bs) mobile H's.

Example 43
N-(6-hydroxy-2-benzoxazolyl)-O-[4-oxo-4-[(1,4,5,6-tetrahydro-2-pyrimidinyl)amino]butyl]-L-tyrosine NMR (DMSO) 1.80 (m) 2HNH—CH2-CH2-CH2-NH; 1.93 (m) 2HCO—CH2-CH2-CH2-O; 2.39 (bt) 2HCO—CH2; 2.93 and 3.12 (2dd) 2H Ph-CH2; 3.24 (bt) 4HNH—CH2-CH2-CH2-NH; 3.90 (bt) 2HCH2-O; 4.19 (bd) 1H Ph-CH2-CH—NH; 6.52 (dd) 1H (H in meta position of the nitrogen); 6.71 and 7.09 (AA'BB') 4H-Ph-; 6.72 (d) 1H (H in ortho position of the oxygen); 6.97 (d) 1H (H in ortho position of the nitrogen); 7.38 (bd) 1H (NH—CH).

Example 44
N-(2-benzoxazolyl)-3-[[4-[3-oxo-3-[(1,4,5,6-tetrahydro-2-pyrimidinyl)amino]propyl]benzoyl]amino]-L-alanine NMR (DMSO) 1.85 (m) 2HNH—CH2-CH2-CH2-NH; 2.76(bt) 2HCO—CH2-CH2-Ph; 2.92 (bt) 2HCO—CH2-CH2-Ph; 3.35 (bs) 4HNH—CH2-CH2-CH2-NH; 3.78 (m) 2HNH—CH2-CH; 4.53 (m) 1HNH—CH2-CH; 6.99 (bt) and 7.11 (bt) 2H (aromatic H's); 7.25 (bd) and 7.35 (bd) 2H (aromatic H's); 7.31 and 7.77 (AA'BB') -Ph-; 8.28 (bd) 1H (NH—CH); 9.02 (bs) 2H (NH-CH2); 11.63 (bs) and 12.89 (bs) mobile H's.

Example 45
N-(7-fluoro-2-benzoxazolyl)-3-[[4-[3-oxo-3-[(1,4,5,6-tetrahydro-2-pyrimidinyl)-amino]-propyl]-benzoyl]-amino]-L-alanine NMR (DMSO) 1.82 (bs) 2HNH—CH2-CH2-CH2-NH; 2.62 (bt) 2HCO—CH2-CH2-Ph; 2.83 (bt) 2HCO—CH2-CH2-Ph; 3.30 (bs) 4HNH—CH2-CH2-CH2-NH; 3.74 (m) 2HNH—CH2-CH; 4.37 (m) 1HNH—CH2-CH; 6.90 (m) and 7.06 to 7.28 (m) 3H (aromatic H's); 7.18 and 7.70 (AA'BB') 4H -Ph-; 8.28 (bs) 1H (NH—CH); 10.20 (bs) and 13.50 (bs) 3H (mobile H's).

Example 46
N-(7-fluoro-2-benzoxazolyl)-O-[4-oxo-4-[(5-hydroxy-1,4,5,6-tetrahydro-2-pyrimidinyl)amino]butyl]-L-tyrosine The compound of Example 46 is prepared in the following manner:

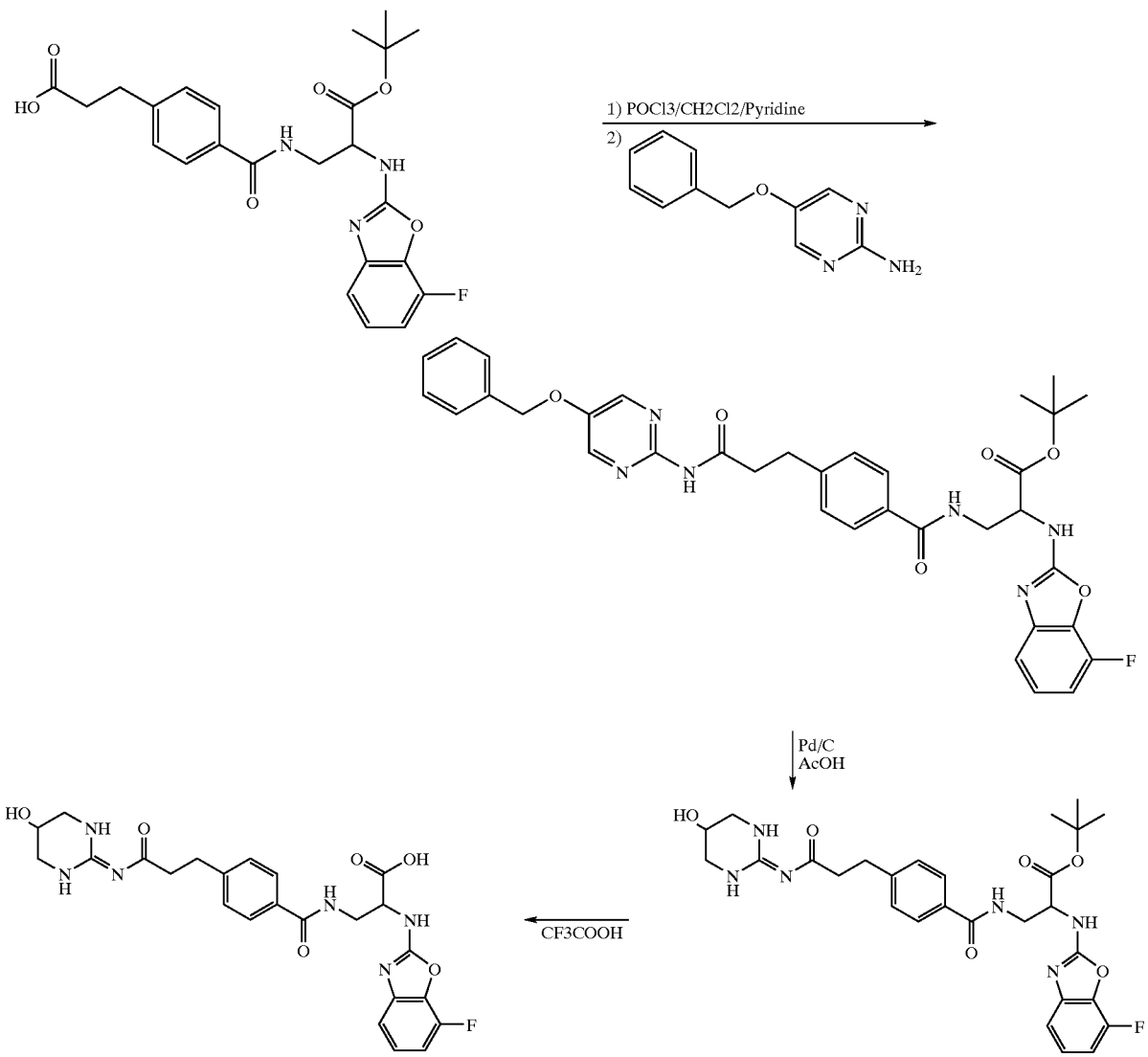

Collect.Czech.Chem.Commun. (1973). 38(5), 1371–80

NMR (DMSO) 1.98 (m) 2HCO—CH2-CH2-CH2-O; 2.56 (m) 2HCO—CH2; 2.91 and 3.15 (2dd) 2H Ph-CH2; 3.29 and 3.35 (2m) 4HNH—CH2-CH2-CH2-NH; 3.95 (bt) 2HCH2-O; 4.10 (bs) 1HNH—CH2-CH-CH2-NH; 4.37 (ddd) 1H Ph-CH2-CH—NH; 6.83 and 7.23 (AA'BB') 4H-Ph-; 6.91 (ddd) 1H (aromatic H); 7.10 (m) 2H (aromatic H's); 8.66 (d) 1H (HN—CH); 8.94 (bs) 2H (NH-CH2); 11.58 (s) and 12.98 (bs) 2H mobile H's Pharmacological Test Kistrin/Vitronectin Receptor ($\alpha_v\beta_3$) ELISA Test Protocol 96-well MaxiSorp planes are coated overnight at 40° C. with 100 µl of Kistrin at 1 µg/ml (dilution in a coating buffer: carbonate 0.05 M/NaOH pH 9.6). The next day, the wells are emptied and the ligands (kistrin) are then fixed (fixing buffers: PBS containing 0.5% BSA (pH=7.4)) for 1 hour at ambient temperature with gentle agitation at 125 rpm. The wells are washed six times (washing buffer: PBS containing 0.05% of Tween 20 (pH 7.7) then the following are added per well and in this order:

40 µl of incubation buffer

10 µl of the dilution of the product to be tested (the products are diluted in a 50:50 mixture DMSO/Water)

50 µl of human $\alpha_v\beta_3$ receptor (cf Pytella et al. Methods Enzymol. (1987) 144 (Dilution in incubation buffer, to be adapted according to the receptor batch and according to the ligand). The ligand, the $\alpha_v\beta_3$ receptor and the products to be studied are co-incubated for 3 hours at ambient temperature with gentle agitation at 125 rpm.

The wells are again washed six times, then incubated for 2 hours at ambient temperature with gentle agitation at 125 rpm, in the presence of 100 µl of anti-receptor antibody conjugated to a peroxidase (The 4B12-HRP antibody is diluted in an incubation buffer (50 mM TRIS pH 7.4; 0.5% BSA; 0.05% Tween 20; 1 mM $MnCl_2$; 50 µM $CaCl_2$; 50 µM $MgCl_2$; 100 mM NaCl) The dilution is adapted according to the receptor batch.

The wells are then washed six times before measuring the ligand-receptor bond carried out using a peroxidase developer kit (TBM Microwell Peroxidase Substrate System Kirkegaard; Cat. Ref. 50-76-00).

This kit contains a bottle A of substrate (3,3',5,5'-tetramethylebenzidine at 0.4 g/l) and a bottle B ($H_2O_2$ at 0.02% in a Citrate/Citric acid buffer). Extemporaneously, a volume of A is mixed with a volume of B, then the reaction mixture is distributed at a rate of 100 µl/well.

The enzymatic reaction develops between 6 and 10 minutes for Kistrin/α$_v$β$_3$ then its evolution is stopped by the addition of 100 μl of 1M phosphoric acid. The optical density is determined at 450 nm.

Expression of the Results

The following curve is plotted: the bond percentage as a function of the logarithm of each concentration of the tested product.

For each product, the IC50 is determined according to the following formula: IC50=(B0+Bmin)/2

B0=Maximum bond in the absence of any product

Bmin =Minimum bond in the presence of the highest concentration of the product.

| EXAMPLE | K/VnR IC$_{50}$ (nM) |
|---|---|
| 1 | 9 |
| 2 | 70 |
| 3 | 50 |
| 4a | 19 |
| 4b | 14 |
| 5 | 15 |
| 6 | 5 |
| 7 | 6 |
| 8 | 8 |
| 9 | 9 |
| 10 | 6 |
| 11 | 7 |
| 12 | 9 |
| 13 | 7 |
| 14 | 7 |
| 15 | 5 |
| 16 | 9 |
| 17 | 9 |
| 18 | 11 |
| 19 | 6 |
| 20 | 35 |
| 21 | 6 |
| 22 | 8 |
| 23 | 10 |
| 27 | 12 |
| 28 | 7 |
| 29 | 10 |
| 30 | 7 |
| 31 | 5 |
| 32 | 10 |
| 33 | 7 |
| 34 | 18 |
| 35 | 18 |

What is claimed is:

1. A compound of the formula

R$_1$—Y—A—B—D—E—F—G wherein

R$_1$ is optionally hydrogenated pyrimidine, Y is —NR$_2$—, A is

unsubstituted or substituted on both sides by alkylene of up to 8 carbon atoms, B is a single bond or alkylene up to 8 carbon atoms, D and F are individually selected from the group consisting of a single bond, alkylene of up to 8 carbon atoms and —O—, E is phenyl unsubstituted or substituted with at least one member selected from the group consisting of alkyl of 1 to 8 carbon atoms, alkoxy of 1 to 8 carbon atoms, hydroxy, halogen, —NO$_2$, —NH$_2$, —CF$_3$, methylene dioxy, —CN, aminocarbonyl, carboxy, alkoxycarbonyl of 2 to 5 carbon atoms, phenyl, phenoxy, benzyl and benzyloxy, G is

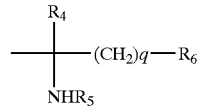

q is 0 or 1,

R$_2$ is selected from the group consisting of hydrogen, (C$_1$–C$_8$)-alkyl-unsubstituted or substituted by at least one halogen, (C$_3$–C$_{12}$)-cycloalkyl-, (C$_3$–C$_{12}$)-cycloalkyl-(C$_1$–C$_8$)-alkyl-, (C$_5$–C$_{14}$)aryl-, (C$_5$–C$_{14}$)-aryl-(C$_1$–C$_8$)-alkyl, —NH$_2$, (R$_8$O)R$_8$NR$_7$—, R$_8$OR$_7$—, R$_8$OC(O)R$_7$, R$_8$—(C$_5$–C$_{14}$)-aryl-R$_7$—, R$_8$R$_8$NR$_7$—, HO—(C$_1$–C$_8$)alkyl-NR$_8$—R$_7$, R$_8$R$_8$NC(O)R$_7$—, R$_8$C(O)NR$_2$R$_7$—, R$_8$C(O)R$_7$—, R$_8$R$_8$N—C(=NR$_8$)—, R$_8$R$_8$N—C(=NR$_8$)—NR$_2$—, (C$_1$–C$_{18}$)-alkylcarbonyloxy-, and (C$_1$–C$_6$)-alkyloxycarbonyl-;

R$_4$ is selected from the group consisting of H, fluorine, (C$_1$–C$_8$)-alkyl-, (C$_3$–C$_{12}$)-cycloalkyl-(C$_1$–C$_8$)alkyl-, (C$_5$–C$_{14}$)-aryl, (C$_5$–C$_{14}$)-aryl-(C$_1$–C$_8$)alkyl-, the alkyls are unsubstituted or substituted by at least one fluorine;

R$_5$ is a monocyclic or polycyclic system, each ring having 4 to 10 aromatic or non-aromatic members, the ring or at least one of the rings having 1 to 4 heteroatoms selected from the group consisting of N, O or S, substituted or unsubstituted by R$_{10}$, R$_{11}$, R$_{12}$ and R$_{13}$;

R$_6$ is selected from the group consisting of —C(O)R$_9$, —C(S)R$_9$, S(O)$_n$R$_9$, P(O)(R$_9$)$_n$, or a heterocycle with 4 to 8 members having 1 to 4 heteroatoms selected from the group consisting of N, O and S;

R$_7$ is a direct bond or a (C$_1$–C$_8$)-alkylene-;

R$_8$ is selected from the group consisting of H, (C$_1$–C$_8$)-alkyl-, (C$_3$—C$_{12}$)-cycloalkyl-, (C$_3$–C$_{12}$)-cycloalkyl-(C$_1$–C$_8$)alkyl-, (C$_5$–C$_{14}$)-aryl, and (C$_5$–C$_{14}$)-aryl-(C$_1$–C$_8$)-alkyl, the alkyls are unsubstituted or substituted by at least one fluorine;

R$_9$ is selected from the group consisting of —OH, (C$_1$–C$_8$)-alkoxy-, (C$_5$–C$_{14}$)-aryl-(C$_1$–C$_8$)alkyloxy-, (C$_5$–C$_{14}$)-aryloxy-, (C$_1$–C$_8$)-alkylcarbonyloxy(C$_1$–C$_4$) alkyloxy-, (C$_5$–C$_{14}$)-aryl-(C$_1$–C$_8$)-alkylcarbonyloxy (C$_1$–C$_4$)alkyloxy-, —NH$_2$, mono or di-(C$_1$–C$_8$-alkyl)-amino-, (C$_5$–C$_{14}$)-aryl-(C$_1$–C$_8$-)alkylamino-, (C$_1$–C$_8$) dialkylaminocarbonyl methyloxy-, (C$_5$–C$_{14}$)-aryl-(C$_1$–C$_8$)-dialkylaminocarbonyl methyloxy-, (C$_5$–C$_{14}$) arylamino- and a D or L amino acid remainder R$_{10}$, R$_{11}$, R$_{12}$, R$_{13}$, are individually selected from the group consisting of H, (C$_1$–C$_8$)-alkyl-unsubstituted or substituted by at least one halogen, (C$_3$–C$_{12}$)-cycloalkyl-, (C$_3$–C$_{12}$)-cycloalkyl-(C$_1$–C$_8$)-alkyl-, (C$_5$–C$_{14}$)-aryl-, (C$_5$–C$_{14}$)-aryl-(C$_1$–C$_8$)-alkyl-, —NH$_2$, (R$_8$O)R$_8$NR$_7$—, R$_8$OR$_7$—, R$_8$OC(O)R$_7$, R$_8$—(C$_5$–C$_{14}$)-aryl-R$_7$—, R$_8$R$_2$NR$_7$—, HO—(C$_1$–C$_8$)alkyl-NR$_2$—R$_7$, R$_8$R$_2$NC(O)R$_7$—, R$_8$C(O)NR$_2$R$_7$—, R$_8$C(O)R$_7$—, R$_2$R$_3$N—C(=NR$_2$)—, —R$_2$R$_3$N—C(=NR$_2$)—NR$_2$—, =O, =S, halogen, —NO$_2$; R$_8$SO$_2$R$_7$—, R$_8$NHSO$_2$R$_7$— and R$_8$R$_2$NSO$_2$R$_7$—.

2. A compound of claim 1 having the formula (Ia)

wherein D' is oxygen or a single bond, F' is —CH$_2$— and p is 1 to 8.

3. A compound of claim 1 having the formula (Ib)

wherein D' is oxygen or a single bond, R' is —CH$_2$— and p is 1 to 8.

4. A compound of claim 1 wherein G is

—CH(NHR$_5$)—CO$_2$H and, R$_5$ is defined as in claim 1.

5. A compound of claim 1 wherein R$_5$ is a heterocycle selected from the group consisting of unsubstituted or substituted by R$_{10}$, R$_{11}$, R$_{12}$ or R$_{13}$ as defined in claim 1.

6. A compound of claim 1 wherein
Y is —NH—
B is selected from the group consisting of a single bond, —CH$_2$—, and —CH$_2$CH$_2$—;
D and F are individually selected from the group consisting of a single bond, —CH$_2$—, —CH$_2$CH$_2$—, and —O—, —NHCO—, —NHCONH—, —O—C(O)—, —C(O)—O—, —CO—, —SO$_2$—, —SO$_2$NH—, —NHSO$_2$—, —S—, —CH=CH—, —C≡C, and —CH(OH)—;
E is phenyl unsubstituted or substituted by R$_{10}$, R$_{11}$, R$_{12}$ and R$_{13}$ and
G is —CH(NHR$_5$)—COOH.

7. A compound of claim 2 wherein D' is a single bond, and p is between 2 and 5.

8. A compound of claim 1 wherein R$_5$ is a heterocycle selected from the group consisting of substituted by at least one phenyl, benzyl, chlorine, bromine, fluorine, nitro, carboxy, methyloxycarbonyl, phenylaminosulfonyl, methylphenylamino-sulfonyl, (C$_1$–C$_2$-alkyl unsubstituted or substituted by at least one chlorine, bromine or fluorine.

9. A compound of claim 1 selected from the group consisting of

N-[1-(phenylmethyl)-1H-tetrazol-5-yl]-O-[3-(5,6,7,8-tetrahydro-1,8-naphthyridin-2-yl)propyl]-L-tyrosine;
N-(2-benzothiazolyl)-O-[3-(5,6,7,8-tetrahydro-1,8-naphthyridin-2-yl)propyl]-L-tyrosine;
N-(2-benzoxazolyl)-O-[3-(5,6,7,8-tetrahydro-1,8-naphthyridin-2-yl)propyl]-L-tyrosine;
N-[5-methoxy-1H-benzimidazol-2-yl]-O-[4-oxo-4-[(1,4,5,6-tetrahydro-2-pyrimidinyl)amino]butyl]-L-tyrosine;
N-[5-methyl-1H-benzimidazol-2-yl]-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-[1-(phenylmethyl)-1H-tetrazol-5-yl]-L-tyrosine;
N-(2-benzoxazolyl)-O-[4-oxo-4-[(1,4,5,6-tetrahydro-2-pyrimidinyl)amino]butyl]-L-tyrosine;
N-(2-benzothiazolyl)-O-[4-oxo-4-[(1,4,5,6-tetrahydro-2-pyrimidinyl)amino]butyl]-L-tyrosine;
N-[6-bromo-2-benzothiazolyl]-O-[4-oxo-4-[(4,5,6-tetrahydro-2-pyrimidinyl)amino]butyl]-L-tyrosine;
N-(5-bromo-7-fluoro-2-benzoxazolyl)-O-[4-oxo-4-[(1,4,5,6-tetrahydro-2-pyrimidinyl)amino]butyl]-L-tyrosine;
N-(5-bromo-2-benzoxazolyl)-3-[(4-[3-oxo-3-[(1,4,5,6-tetrahydro-2-pyrimidinyl)amino]propyl]benzoyl]amino]-L-alanine;
N-(6-bromo-2-benzothiazolyl)-3-[[4-[3-oxo-3-[(1,4,5,6-tetrahydro-2-pyrimidinyl)amino]propyl]benzoyl]amino]-L-alanine;
N-(7-fluoro-2-benzoxazolyl)-O-[4-oxo-4-[(1,4,5,6-tetrahydro-2-pyrimidinyl)amino]butyl]-L-tyrosine;
N-(6-fluoro-2-benzoxazolyl)-O-[4-oxo-4-[(1,4,5,6-tetrahydro-2-pyrimidinyl)amino]butyl]-L-tyrosine;
N-(5-fluoro-2-benzoxazolyl)-O-[4-oxo-4-[(1,4,5,6-tetrahydro-2-pyrimidinyl)amino]butyl]-L-tyrosine;
N-(7-chloro-2-benzoxazolyl)-O-[4-oxo-4-[(1,4,5,6-tetrahydro-2-pyrimidinyl)amino]butyl]-L-tyrosine;
N-(6-chloro-2-benzoxazolyl)-O-[4-oxo-4-[(1,4,5,6-tetrahydro-2-pyrimidinyl)amino]butyl]-L-tyrosine;
N-(5-chloro-2-benzoxazolyl)-O-[4-oxo-4-[(1,4,5,6-tetrahydro-2-pyrimidinyl)amino]butyl]-L-tyrosine;

N-(5-bromo-2-benzoxazolyl)-O-[4-oxo-4-[(1,4,5,6-tetrahydro-2-pyrimidinyl)amino]butyl]-L-tyrosine;
N-(naphth[2,3-d]oxazol-2-yl)-O-[4-oxo-4-[(1,4,5,6-tetrahydro-2-pyrimidinyl)amino]butyl]-L-tyrosine;
N-(naphth[1,2-d]oxazol-2-yl)-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-(5-phenyl-2-benzoxazolyl)-L-tyrosine;
N-(6-nitro-2-benzoxazolyl)-O-[4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-[5-(trifluoromethyl)-2-benzoxazolyl]-L-tyrosine;
N-(oxazolo[5,4-b]pyridin-2-yl)-O-[4-oxo-4-[(1,4,5,6-tetrahydro-2-pyrimidinyl)amino]butyl]-L-tyrosine;
N-(oxazolo[4,5-b]pyridin-2-yl)-O-(4-oxo-4-[(1,4,5,6-tetrahydro-2-pyrimidinyl)amino]butyl]-L-tyrosine;
O-[4-oxo-4-[(1,4,5,6-tetrahydro-2-pyrimidinyl)amino]butyl]-N-[5-(trifluoromethyl)-oxazolo[4,5-b]pyridin-2-yl]-L-tyrosine;
N-(6,7-difluoro-2-benzoxazolyl)-O-[4-oxo-4-[(1,4,5,6-tetrahydro-2-pyrimidinyl)amino]butyl]-L-tyrosine;
N-(5,7-dichloro-2-benzoxazolyl)-O-[4-oxo-4-[(1,4,5,6-tetrahydro-2-pyrimidinyl)amino]butyl]-L-tyrosine;
N-(5,7-dichloro-6-methyl-2-benzoxazolyl)-O-[4-oxo-4-[(1,4,5,6-tetrahydro-2-pyrimidinyl)amino]butyl]-L-tyrosine;
N-[5-[(phenylamino)sulphonyl]-2-benzoxazolyl]-O-[4-oxo-4-[(1,4,5,6-tetrahydro-2-pyrimidinyl)amino]butyl]-L-tyrosine;
N-[5-[(N-methylphenylamino)sulphonyl]-2-benzoxazolyl]-O-[4-oxo-4-[(1,4,5,6-tetrahydro-2-pyrimidinyl)amino]butyl]-L-tyrosine;
N-(6-chloro-2-benzothiazolyl)-O-[4-oxo-4-[(1,4,5,6-tetrahydro-2-pyrimidinyl)amino]butyl]-L-tyrosine;
N-(7-bromo-2-benzothiazolyl)-O-[4-oxo-4-[(1,4,5,6-tetrahydro-2-pyrimidinyl)amino]butyl]-L-tyrosine;
N-(5-bromo-2-benzothiazolyl)-O-[4-oxo-4-[(1,4,5,6-tetrahydro-2-pyrimidinyl)amino]butyl]-L-tyrosine;
N-(1H-benzimidazol-2-yl)-O-[4-oxo-4-[(1,4,5,6-tetrahydro-2-pyrimidinyl)amino]butyl]-L-tyrosine;
N-(5-nitro-2-benzoxazolyl)-O-[4-oxo-4-[(1,4,5,6-tetrahydro-2-pyrimidinyl)amino]butyl]-L-tyrosine;
N-(4-nitro-2-benzoxazolyl)-O-[4-oxo-4-[(1,4,5,6-tetrahydro-2-pyrimidinyl)amino]butyl]-L-tyrosine;
N-(6-ethylsulphonyl-2-benzoxazolyl)-O-[4-oxo-4-[(1,4,5,6-tetrahydro-2-pyrimidinyl)amino]butyl]-L-tyrosine;
N-(4,5,6,7-tetrafluoro-2-benzoxazolyl)-O-[4-oxo-4-[(1,4,5,6-tetrahydro-2-pyrimidinyl)amino]butyl]-L-tyrosine;
N-(4-methyl-2-benzoxazolyl)-O-[4-oxo-4-[(1,4,5,6-tetrahydro-2-pyrimidinyl)amino]butyl]-L-tyrosine;
N-(5-methoxy-2-benzoxazolyl)-O-[4-oxo-4-[(1,4,5,6-tetrahydro-2-pyrimidinyl)amino]butyl]-L-tyrosine;
N-(4-hydroxy-2-benzoxazolyl)-O-[4-oxo-4-[(1,4,5,6-tetrahydro-2-pyrimidinyl)amino]butyl]-L-tyrosine;
N-(6-hydroxy-2-benzoxazolyl)-O-[4-oxo-4-[(1,4,5,6-tetrahydro-2-pyrimidinyl)amino]butyl]-L-tyrosine;
N-(2-benzoxazolyl)-3-[[4-[3-oxo-3-[(1,4,5,6-tetrahydro-2-pyrimidinyl)amino]propyl]benzoyl]amino]-L-alanine;
N-(7-fluoro-2-benzoxazolyl)-3-[[4-[3-oxo-3-[(1,4,5,6-tetrahydro-2-pyrimidinyl)amino]propyl]benzoyl]amino]-L-alanine and
N-(7-fluoro-2-benzoxazolyl)-O-[4-oxo-4-[(5-hydroxy-1,4,5,6-tetrahydro-2-pyrimidinyl)amino]butyl]-L-tyrosine.

10. A process for the preparation of a compound of claim 1 comprising the coupling of two or more fragments which can be derived by retrosynthesis of a compound of formula (I).

11. The process of claim 10 wherein a carboxylic acid or a carboxylic acid of the formula

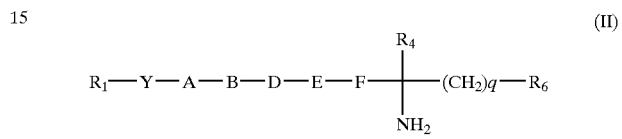

wherein $R_1$, Y, A, B, D, E, F, $R_4$, $R_6$ and q are as defined in claim 1, and where, optionally, the functional groups are in the form of precursors or in protected form, is reacted with a heterocycle of the formula:

$R_5$-Hal or $R_5$—SMe wherein $R_5$ is as defined in 1 and Hal is halogen, and where, optionally, the functional groups are in the form of precursors or in protected form, said functional groups optionally present in the form of a precursor or in protected form, then subsequently converting the precursor or protected into groups present in the compound of formula (I).

12. A composition for treating osteoporosis comprising an osteoporosisly effective amount of a compound of claim 1 and an inert pharmaceutical carrier.

13. A method for treating osteoporosis in warm-blooded animals comprising administering to warm-blooded animals in need thereof an amount of a compound of claim 1 sufficient to treat osteoporosis.

14. A method of inhibiting activity on bone resorption in warm-blooded animals comprising administering to warm-blooded animals in need thereof an amount of a compound of claim 1 sufficient to inhibit activity on bone resorption.

15. A method of inhibiting tumor growth or cancerous metastases in warm-blooded animals comprising administering to warm-blooded animals in need thereof cancer inhibiting amount of a compound of claim 1.

16. A method of treating inflammation in warm-blooded animals comprising administering to warm-blooded animals in need thereof an anti-inflammatorily effective amount of a compound of claim 1.

* * * * *